United States Patent [19]

Wong et al.

[11] Patent Number: 5,370,114

[45] Date of Patent: Dec. 6, 1994

[54] NON-INVASIVE BLOOD CHEMISTRY MEASUREMENT BY STIMULATED INFRARED RELAXATION EMISSION

[76] Inventors: Jacob Y. Wong, 4589 Camino Molinero, Santa Barbara, Calif. 93110; Bent Formby, 1625 Overlook La., Santa Barbara, Calif. 93103; Charles M. Peterson, 1075 San Antonio Creek Rd., Santa Barbara, Calif. 93111

[21] Appl. No.: 852,085

[22] Filed: Mar. 12, 1992

[51] Int. Cl.$^5$ .............................................. A61B 6/00
[52] U.S. Cl. ................................... 128/633; 128/664; 356/39
[58] Field of Search ............... 128/633, 634, 664, 665; 356/39–41

[56] References Cited

U.S. PATENT DOCUMENTS

| | | | |
|---|---|---|---|
| 3,412,729 | 11/1968 | Smith, Jr. | 128/633 |
| 3,830,222 | 8/1974 | Chance | 128/665 |
| 3,958,560 | 5/1976 | March . | |
| 3,963,019 | 6/1976 | Quandt . | |
| 4,014,321 | 3/1977 | March . | |
| 4,055,768 | 10/1977 | Bromberg | 250/461 |
| 4,704,029 | 11/1987 | Van Heuvelen | 356/39 |
| 4,882,492 | 11/1989 | Schlager | 250/346 |
| 4,901,728 | 2/1990 | Hutchinson | 128/633 |
| 4,968,887 | 11/1990 | Wong | 250/343 |
| 5,009,230 | 4/1991 | Hutchinson | 128/633 |
| 5,028,787 | 7/1991 | Rosenthal | 250/341 |
| 5,054,487 | 10/1991 | Clarke | 128/633 |
| 5,115,133 | 5/1992 | Knudson | 250/341 |
| 5,183,042 | 2/1993 | Harjunmaa et al. | 128/633 |

FOREIGN PATENT DOCUMENTS

3801158A1 7/1989 Germany .

OTHER PUBLICATIONS

Yitzhak Mendelson, *Blood Glucose Measurement by Multiple* . . . pp. 458–464, May 1990.
H. Zeller, *Blood glucose measurement by infrared* . . . pp. 129–134, 1989.

*Primary Examiner*—Angela D. Sykes
*Attorney, Agent, or Firm*—John A. Frazzini

[57] ABSTRACT

An apparatus for measuring the concentration of a selected solute in a solution. This apparatus is particularly suitable for measuring the concentration of blood components, such as blood glucose. A beam of exposing light is imaged through a wall of a containment vessel onto a region of the sample adjacent to this wall to induce from said selected solute emission of light that includes at least one emission peak that can be used to calculate the concentration of this solute. At least one detector is positioned to maximize the strength of detected signal, if other components of this solution strongly absorb the emitted light. The exposing light is directed such that the detected signal is maximized as a function of the path of this exposing light. A particular embodiment is a non-invasive blood glucose tester that can be used painlessly by diabetics to monitor their blood glucose levels. In this embodiment, the containment vessel is preferably one of the patient's fingers. At least two additional detected signals are monitored and processed at wavenumbers suitable for eliminating temperature and pressure effects on the calculated blood glucose levels.

29 Claims, 10 Drawing Sheets

NON-INVASIVE BLOOD CHEMISTRY MEASUREMENT BY STIMULATED INFRARED RELAXATION EMISSION

FIELD OF THE INVENTION

This invention relates in general to medical instrumentation, and more particularly to the field of non-invasive blood chemistry measurements, such as measurements of blood glucose concentration levels.

Convention Regarding Reference Numerals

In the figures, the first digit of a reference numeral indicates the first figure in which is presented the element indicated by that reference numeral.

BACKGROUND OF THE INVENTION

An estimated 14 million Americans have diabetes, a disease in which the body does not produce or respond properly to insulin. The resulting high blood glucose concentration levels (also referred to as blood glucose level or blood-sugar levels) can cause severe damage to the heart, blood vessels, kidneys, eyes and nerves. If untreated, diabetes can lead to death in an unexpectedly short period of time. People with diabetes must balance diet, exercise and medication (e.g., insulin, which can be taken orally or by injections) in order to maintain their blood glucose levels as close as possible to normal levels. Insulin pumps have been developed to enable continuous administration of insulin to a diabetic.

Regardless how insulin is administered to a diabetic, it is very important to continually monitor the blood glucose level to avoid the problems that arise from low glucose levels as well as those that arise from excessive glucose levels. Therefore, diabetics have to test their blood glucose levels frequently (as often as six times a day) in order to maintain a proper level of insulin in their blood.

Several different techniques have been developed for measuring blood glucose concentration levels. A change in blood glucose level affects the index of refraction and the absorbance spectrum of the blood. For example, in U.S. Pat. No. 4,704,029, discussed in more detail below, this change in the index of refraction of blood alters the fraction of light reflected at an interface in contact with the blood being tested. This technique is not amenable to a non-invasive method of detecting a person's blood glucose level. Several references, discussed below, utilize absorbance spectroscopy to measure the glucose concentration in a patient's blood. Unfortunately, because of the strong level of absorption of water at the wavelength of infrared absorption peaks for blood glucose, these techniques result in small output signals so that there is a smaller than desired signal-to-noise ratio for such tests.

Infrared absorption spectroscopy has long been used for the identification of unknown organic and biological substances in aqueous solutions. This technique is based upon the fact that all molecules exhibit, to some extent, their own unique oscillatory motions characterized by specific resonance absorption peaks in the infrared portion of the electromagnetic spectrum. These characteristic absorption peaks are caused by the resonant vibrational and rotational oscillations of the molecules themselves. In several references discussed in more detail below, absorption spectra are used to monitor changes in blood glucose levels. These resonant vibrational modes can also be utilized to implement fluorescence techniques for measuring blood glucose levels.

In U.S. Pat. No. 4,055,768 entitled *Light Measuring Apparatus* issued to Nathan S. Bromberg on Oct. 25, 1977, the level of zinc protoporphyrin in blood is detected by smearing a blood sample on a slide and illuminating this sample with pulsed light that induces fluorescent emission from the zinc protoporphyrin. Synchronous detection is used to measure the intensity of the pulsing fluorescent light emitted from these zinc protoporphyrin molecules.

In U.S. Pat. No. 4,704,029 entitled *Blood Glucose Monitor*, issued to Alan Van Heuvelen, a blood glucose monitor is presented that is particularly applicable for use as an implant for controlling an insulin pump. This glucose monitor measures the glucose level of blood by utilizing a refractometer which measures the index of refraction of blood adjacent to an interface with a transparent surface of the refractometer. Within this implanted monitor, light is directed at a transparent interface that is in contact with the diabetic's blood. The angle of incidence is near the critical angle of total internal reflection, so that the small changes in the index of refraction of blood caused by changes in the blood glucose level will significantly alter the fraction of light reflected from this surface. In order to eliminate a similar change in the amount of reflected light due to changes in the concentration of albumin in the diabetic's blood, two light beams of unequal wavelengths are each directed at the interface at an angle near it's associated critical angle.

The problem with this proposed technique is that it is not specific. The index of refraction of blood is affected by numerous chemical substances in blood, only one of which is the blood glucose level. Therefore, a change in this index of refraction may not indicate a change in the blood glucose level.

The usual procedure for testing blood glucose levels involves pricking a finger to obtain a small sample of blood for analysis. In addition to the unwelcome pain, frequent finger-pricks of a person with diabetes can produce inflammation and/or callousing of that person's fingers. Unfortunately, although the frequent finger pricks are avoided by use of an implanted monitor, not only must the diabetic be subjected to the discomfort of implanting such a monitor, these monitors are often attacked by the body in a manner that degrades device operation. Because of this, the diabetic might require a succession of such implants. Thus, a portable, non-invasive, inexpensive, reliable blood glucose sensor is badly needed to enable diabetics to take better care of themselves without having to draw blood each time they need to check their blood glucose levels.

Over the years, many purportedly non-invasive methods of monitoring blood glucose have been proposed. For example, in the following three U.S. patents, a light beam is directed through a person's eye to monitor that person's blood glucose level. In U.S. Pat. No. 3,963,019 entitled *Ocular Testing Method and Apparatus* issued to Quandt on Jun. 15, 1976, a beam of polarized light is directed through the aqueous humor of the person's eye to measure that person's blood glucose level. The fraction of this light that is absorbed during transit through that person's eye indicates the glucose level in the blood.

In U.S. Pat. No. 3,958,560 entitled *Non-Invasive Automatic Glucose Sensor System*, issued on May 25, 1976 to Wayne Front March, an infrared light source, mounted on a scleral contact lens, transmits 0.975 micron, infrared light through this contact wearer's cornea and aqueous humor to an infrared detector, also mounted on this lens. This wavelength is used because it is absorbed strongly by the hydroxyl in glucose. Test results are transmitted to a receiver mounted on or near this person, thereby providing nearly continuous monitoring of that person's blood glucose level. For example, a test can be initiated each time a person blinks.

In U.S. Pat. No. 4,014,321 entitled *Non-invasive Glucose Sensor System* issued to Wayne Front March on Mar. 29, 1977, a polarized beam of light is directed through a person's eye and the blood glucose level is determined from the amount that this polarized light is rotated by passage through this person's eye.

There are several disadvantages of using a person's eye as the target for blood glucose measurements. Considerable care must be exercised to prevent physical damage to the eye. The scleral contacts, containing blood chemistry test equipment, can be uncomfortable to the wearer. Professional care is required if insertion of an object into the eye is part of the measurement routine, such as is the case in U.S. Pat. No. 3,963,019 cited above. Such a blood glucose monitor would not be desirable for diabetic patients who have to measure their own blood glucose levels daily.

The following references describe blood glucose monitors that inject a beam of light through a person's skin to interact with the blood adjacent to the skin.

German Offenlegungsschrift DE 38 01 158 A1 entitled *Blood Sugar Measuring Apparatus* filed by Marina Struck on Jan. 16, 1988, is a rather confusing application, in which a monochromatic laser transmits a polarized, monochromatic, laser beam, through the skin of a person's finger, apparently for the purpose of rotating glucose molecules in the blood. There is some discussion of this light causing rotation of sugar molecules, some discussion of the polarization being caused by a reflection from the sugar molecules of a proper orientation, some discussion that photons are emitted from excited glucose molecules in the blood and some discussion that this light is tuned to a characteristic wavelength of glucose. This teaching appears to be inconsistent and is so confusing that it does not really teach the true nature of that invention.

In U.S. Pat. No. 4,901,728 entitled *Personal Glucose Monitor* issued to Donald P. Hutchinson on Feb. 20, 1990, two infrared beams are formed which are polarized, respectively, at $+45°$ and $-45°$ relative to a polarizer and, therefore, these two beams normally produce equal intensity output signals. However, when these beams are passed through a person's tissue, such as that person's ear lobe, these polarized beams are rotated by glucose by equal angles, thereby reducing the intensity of one of the output signals and increasing the other. These pulses are chopped so that the detector receives, at any given time, only light from one of these beams.

In recognition of the strong absorption of (long wavelength) infrared radiation by tissue and the effects of other variable parameters associated with tissue such as its thickness, pigmentation, temperature and blood volume etc., this reference recommends the use of two radiation sources which emit infrared light at two different wavelengths. Specifically, this reference uses light beams of wavelength 0.94 microns and 1.3 microns, in what is commonly referred to as the "near-infrared" region (i.e., wavenumber in the range 10,638–7,692 $cm^{-1}$). Hutchinson's proposed intricate optical technique in the monitoring of blood glucose in tissue is rather complicated and requires a number of very delicate and difficult adjustments in its operation. It is therefore not readily amenable to the realization of a reliable, low-cost and rugged blood glucose sensor, such as is badly needed today. It is asserted, without discussion, that the use of an additional pair of analogous beams at different wavelengths enables correction for tissue absorption. U.S. Pat. No. 5,009,230 entitled *Personal Glucose Monitor* issued to Donald P. Hutchinson on Apr. 23, 1991, provides the missing details regarding this correction for tissue absorption.

The following references utilize absorption spectroscopy to detect various blood chemicals:

In the article by H. Zeller, et al entitled *Blood Glucose Measurement by Infrared Spectroscopy*, p. 129–134, (1989), the absorption spectra of blood glucose and some other blood components, are analyzed for the purpose of identifying those wavelength ranges in which accurate measurements of blood glucose can be detected. Differences between absorption spectra for a water-only solution and for a water-plus-glucose solution is observed only in an wavenumber range, referred to therein as the "finger-print region", which extends from 1650 to 800 $cm^{-1}$.

A strong absorption peak, which occurs at a wavelength of 9.02 micron (i.e., wavenumber 1109 $cm^{-1}$), is caused by the stretching vibrations of the endocyclic C—O—C group. Water absorption washes out all glucose spectra in the near infrared (NIR) (i.e., wavenumber in the range 12,500–4,000 $cm^{-1}$) and the mid infrared (MIR) wavelength regions (i.e., wavenumber in the range 4,000–500 $cm^{-1}$), so that, except for the fingerprint region, these regions are not suitable for monitoring blood glucose levels. In the fingerprint region, only glucose and haemoglobin exhibit intense absorption at this wavelength. Only the following five wavenumbers give enough sensitivity for measurement of blood glucose: 1040, 1085, 1109, 1160 and 1365 $cm^{-1}$. Only the 1040 $cm^{-1}$ band is free of superimposed absorption of other blood constituents, and only glucose and haemoglobin exhibit intense absorption at 1109 $cm^{-1}$. Therefore, the most attractive choices for monitoring blood glucose levels are the 1040 and 1109 $cm^{-1}$ absorption bands.

In the article by Yitzhak Mendelson, et al entitled *Blood Glucose Measurement by Multiple Attenuated Total Reflection and Infrared Absorption Spectroscopy*, IEEE Transactions On Biomedical Engineering, Vol. 17, No. 5, May 1990, it is recognized that, of the more than 20 absorption peaks of D-glucose in the 2.5–10 micron range, not all of those peaks are specific to D-glucose. However, the peak at an wavenumber of 640 $cm^{-1}$ is prominent and is due to the carbon-oxygen-carbon bond in the pyrane ring of D-glucose. It is also recognized that, because of the intrinsic high background absorption of water in the infrared wavelength range and the relatively low glucose concentrations in blood, it is important to use a $CO_2$ laser, because it produces a powerful beam having a narrow peak that is effective in detecting such low concentrations. Sensitivity is further increased by using a multiple attenuated total reflection (ATR) to pass the laser beam through the sample several times. Unfortunately, equipment implementing such a laser/ATR technique is very expensive.

Biological molecules, due to their very complicated structures, possess a large number of similar infrared absorption peaks that are often overlapping. For example, the characteristic infrared spectrum of anhydrous D-glucose (ADG) has more than 20 absorption peaks in the wavelength region of 2.5-10 microns as shown in FIG. 1. It is important to note that not all the absorption peaks shown in FIG. 1 are specific to this molecule. The prominent absorption peak around 9.61 microns (1,040 $cm^{-1}$), however, is somewhat specific to the carbon-oxygen—carbon bond of glucose, because of its pyrane ring.

In U.S. Pat. No. 5,028,787 entitled *Non-invasive Measurement of Blood Glucose*, issued to Robert D. Rosenthal on Jul. 2, 1991, a near-infrared quantitative analysis instrument and method are presented that non-invasively measures blood glucose by analyzing near-infrared energy following "interactance" with venous or arterial blood, or transmission through a blood containing body part, such as a finger tip. Because of the strong absorption of long wavelength, infrared radiation by body tissues, only near-infrared radiation of wavelength less than approximately one micron is used. A set of filters are utilized to pass through a sample only wavelengths that are much more strongly absorbed by glucose than by other interfering substances in the blood. The effect is that the interference from these other substances is substantially removed. Because Rosenthal has worked in this field since 1978 without yet producing a commercial non-invasive blood glucose monitor, it appears unlikely that this approach will be successful.

In a closely related U.S. Pat. No. 4,882,492 entitled *Non-Invasive Near Infrared Measurement of Blood Analyte Concentration*, issued to Kenneth J. Schlager on Nov. 21, 1989, an apparatus and related method are disclosed for measuring the concentration of glucose or other blood analytes utilizing both diffuse reflected and transmissive infrared absorption measurements. The wavelengths of exposing radiation are again limited to less than 2 microns. A high intensity light source is utilized as a source to provide sufficient light intensity to penetrate a significant distance into a blood sample. A cell containing only an interfering analyte is placed in the optical path to absorb substantially all of the light in interfering absorption bands, thereby substantially eliminating the interfering spectral components. This has the advantage of allowing transmission of bands of light, outside of those bands that are strongly absorbed by spectrally interfering substances in the blood. This allows more light to pass through the blood sample than is allowed in the Rosenthal approach that only passes a few narrow bands of light.

The same difficulty (i.e., high absorption of water in the wavelength range of exposing light) experienced by Rosenthal over the years in his proposed methods apply also to the teachings of Schlager. The prognosis of a breakthrough in the successful development of a non-invasive blood glucose monitor using near-infrared absorption and related techniques remains at present very much in doubt.

The use of infrared absorption spectroscopy for blood glucose measurement was proposed as early as 1981. This work was actively carried forward by a host of research scientists and physicians during the past decade leading to the above-indicated investigations by Zeller et. al. in 1989 and Mendelson et. al. in 1990. The motivation for such intense efforts in this particular field of research stems from the need for a convenient, inexpensive method of monitoring blood glucose concentration levels.

The use of glucose absorption bands in the near and middle infrared regions for continuous blood glucose measurement appeared very promising in the early years. However, the measurement of physiological concentrations of glucose in blood by conventional infrared absorption spectroscopy has been severely hampered by the intrinsic high background absorption of water in the infrared (see FIG. 2). Despite numerous proposals and attempts, no viable physical measurement technique has yet been developed, that would lead to the realization of a low-cost, non-invasive blood glucose sensor. The most recent proposal by Mendelson et. al. of using a carbon dioxide ($CO_2$) laser as an infrared source in combination with a multiple attenuated total reflection (ATR) technique increases the depth of penetration of an optical beam into the sample, but does not overcome the fundamental problem that the absorption by water far exceeds the absorption by the blood component to be measured.

FIG. 2 illustrates that, in the near to medium infrared regions (i.e., 2-10 micron wavelength light), the absorption coefficient of water exceeds 10 $cm^{-1}$ and reaches as high as 10,000 $cm^{-1}$ at approximately 3 microns. For an absorption coefficient of 100 $cm^{-1}$, 63% of infrared radiation would be absorbed by a mere 0.1 mm layer of water. Since over 80% (by weight) of the human body is water, any device that relies upon the absorption of infrared radiation by blood-glucose in some part of the human body containing blood, would receive too weak a signal to process. Although a high power $CO_2$ laser, operating in the infrared wavelength region, can provide sufficient optical power to penetrate significantly through such a high absorbance medium, the cost of such a coherent source alone renders a low-cost, non-invasive blood-glucose sensor impractical. In addition, the absorption rate by the water in the blood greatly exceeds that for the blood glucose, so that the portion of the absorption signal caused by the blood glucose is much smaller than that for water. The $CO_2$ laser does, however, enable the optical energy to be concentrated within the absorption peak of blood at 1040 $cm^{-1}$, so that sensitivity is at least much better than when a broader band source is utilized. However, an effective blood glucose concentration detector should somehow overcome the above limitation of the blood glucose being much less absorptive in this range than is the water content of blood.

SUMMARY OF THE INVENTION

In accordance with the illustrated preferred embodiments, a method and associated apparatus are presented for a non-invasive method of testing diabetic patients' blood chemistry, such as blood glucose concentration levels. Although this invention is motivated by the need to measure blood glucose concentration levels, it is also applicable to the detection of other blood components. Likewise, although the following particular examples are in terms of blood glucose concentration detection, the design criteria discussed herein are directly applicable to other choices of sample. In particular, this process is also applicable, in its broadest concept, to measurement of the concentration of any selected solute, even when all of its significant absorption peaks are located within a range of wavenumbers in which such light is strongly absorbed by the solvent and/or other solutes. By "strongly absorbed" is meant that the absorption coefficient is greater than 10 $cm^{-1}$).

The sample is exposed by a beam of light that excites molecules of the selected solute into one or more excited states from which they emit light by the process of stimulated infrared relaxation emission. One or more detectors, positioned to receive part of this emitted light, produce an output signal that is indicative of the concentration of the selected solute. The strength of the detector output signal(s) is affected by the following five factors: (i) the fractional absorption of the exposing beam before it reaches the selected solute; (ii) the absorption intensity of the selected solute for the exposing beam; (iii) the emission intensity from the selected solute at the wavenumber to be detected, produced per unit flux of the exposing beam at these solute molecules; (iv) the fraction of this emitted light that reaches the detector; and (v) the sensitivity of the detector for light of the wavenumber of the emitted light.

The source of exposing light, the wavelength of exposing light, the wavelength of the emitted light, the pathlength of the exposing light through the solution, the pathlength of the emitted light through the solution and the detector are chosen to maximize the signal-to-noise ratio of the detected solute concentration. The exposing light is imaged onto a region of the solution adjacent to a wall of a containment vessel containing the solution under test in order to minimize the pathlength of the exposing light. The wavelength range of the exposing light is selected so that the photons of the exposing light have sufficient energy to excite molecules of the selected solute to excited states from which at least one decay path will result in the emission of light at one or more wavelengths that are useful in quantizing the concentration of the selected solute. Preferably, this wavelength range is such that the photons of this exposing light have enough energy to excite the molecules of the selected solute to levels that are closely spaced, so that a range of exposing wavelengths are effective in exciting molecules of the selected solute to excited levels from which there will be decays that produce the desired wavelength of emitted light. This avoids any need to carefully control the wavelength of the exposing light to match any single absorption peak of the selected solute.

One or more detectors, to collect light emitted from the selected solute, are located adjacent to where this light is directed into the containment vessel, thereby substantially minimizing the pathlength of the emitted light from the exposed sample molecules to the detector(s). Preferably, the wavelength of the emitted light that is detected to measure the concentration of the selected solute is such that inexpensive photodetectors are available at this wavelength. This configuration of exposing light beam and detector substantially minimizes the combined pathlength of the exposing light to these emitting solute molecules and the emitted light back to the detector(s). Such substantial minimization of this combined pathlength substantially minimizes the amount of absorption of this light by the solvent and other absorbing solutes at the wavelengths of the exposing and emitted light.

The exposing light is focussed onto a small region of the solution near the source of this light so that the pathlength through the solution is small and so the solid angle subtended by the detector(s) by the light emitted from this region is increased. Such concentration of the beam can be achieved by use of achromatic lenses, but, for low cost embodiments, it is preferable to utilize a substantially monochromatic light source so that achromatic aberrations do not significantly affect the signal to noise ratio of the output signal(s) from the detector(s). Suitable sources include laser diodes and light emitting diodes (in particular, super-radiant light emitting diodes which produce a high intensity of light from an inexpensive light source). High intensity (on the order of 5 Watts/cm$^2$) light sources are useful to produce sufficient intensity that the absorption of light by the solvent and/or other solutes does not unduly degrade the amplitude of the signal(s) from the detector(s). Preferably, the intensity is at least 50 Watts/cm$^2$, so that multiphoton processes can assist in the excitation of the selected solute molecules.

The wavelength of the incident light is preferably in a range that enables it to pass through the walls of the containment vessel containing the solution under test. In the preferred embodiments of the blood chemistry tester, the containment vessel is a portion of the patient's body and is preferably one of patient's fingers, because the patient can easily bring a finger into proper contact with the blood chemistry tester. The wall of such a containment vessel is therefore the epithelium of that person's finger. In this embodiment, the wavelength of the exposing radiation is in the range from 0.6 microns to 1.5 microns, because this range of wavelengths is not strongly absorbed by the epithelium of the patient. Furthermore, skin is one of the driest portions of a human body, so that there will be negligible absorption of the exposing and emitted light as it passes through the epithelium.

Because of the large absorption by water and the other blood components, it is advantageous to expose a blood sample with a very intense beam of light, so that a significant fraction of the selected component molecules are excited. By a "very intense beam" is meant a beam of intensity of at least 5 Watts/cm$^2$. Because of this high intensity, it is advantageous for the molecular bond being excited to be relatively strong, so that the molecules of the selected component which are nearest to the point at which this light beam is directed into the solution will not decompose in significant amounts. It is also preferred that this peak not coincide with an absorption peak of one of the other blood components so that this incident energy is more efficiently coupled into the desired excitation.

The light, that is emitted from the selected solute by stimulated relaxation, exhibits peaks that are substantially similar, but of slightly longer wavelength, than peaks of the absorption spectrum of the selected solute. In the case of anhydrous D-glucose (also referred to as "ADG", "blood glucose", or "blood sugar") concentration measurements, there are five known glucose absorption bands in this range. These bands are centered at wavenumbers 1040, 1085, 1109, 1160 and 1365 cm$^{-1}$. Unfortunately, the following blood components produce significant absorption at the following four of these bands: proteins at 1085 cm$^{-1}$; hemoglobin at 1109 cm$^{-1}$; urea at 1160 cm$^{-1}$ and all CH2 groups at 1365 cm$^{-1}$. Only the 1040 cm$^{-1}$ band does not coincide with any of these other infrared-active, blood components. Therefore, this particular wavenumber is detected to measure the concentration of anhydrous D-glucose (ADG) molecules (otherwise known as blood-sugar) in blood.

The 1040 cm$^{-1}$ absorption band corresponds to absorption by the C—O—C bond of the pyrane ring of blood glucose. This is fortunate, because this bond is particularly durable under optical exposure by visible or shorter wavelength radiation. Therefore, the ADG molecule does not readily break up into parts even under very strong excitation by light. This unique property is attributed to the resiliency of the C—O—C bond of its pyrane ring molecular structure in that the bond can be stretched, squeezed or twisted by light excitation without breaking apart. When the ADG molecule is bombarded by strong radiation of wavelength selected to excite it from its ground state to an excited state, the molecule is much more likely, via absorption of this radiation, to jump into an excited state than to break up into fractional molecular species. This excited molecule subsequently returns to its ground energy state either by elastic or inelastic processes. Because of this durability, the light intensity utilized to measure the blood glucose concentration is larger than would normally be possible, thereby increasing the sensitivity of this particular blood component sensor.

These excited blood glucose molecules can transition to their ground state by inelastic processes, such as collisions with other molecules or walls of a confining structure. In such an inelastic process, the excitation energy is converted primarily into thermal energy. These excited molecules can also transition into their ground state by an elastic process, commonly known as stimulated relaxation emission, in which an excited molecule emits radiation of wavenumber characteristic of that molecule and of slightly longer wavelength than that of the light that excited such molecule. This slight shift in wavelength occurs because of conservation of energy and momentum constraints on the transition.

This incident light preferably has a very narrow bandwidth, such as occurs in laser light, because such narrow bandwidth enables the light to be focussed by inexpensive optical components into a very narrow region (about 50 micron diameter), just inside the dermal layer and on the top part of the papillary bed that is closest to the epidermis. This location for focussing the beam is selected because it is a region having a large concentration of blood and because it is closely spaced (about 3 microns) from the epithelium. Thus, the light produced by stimulated, relaxation emission of the excited glucose molecules, need traverse only a very short distance from this focal region to a detector located in contact with the epidermis. Preferably, the portion of the epidermis through which this light is directed is on the front side of a finger (i.e., the side away from the nail) because this produces a particularly easy embodiment for a diabetic to use. The diabetic need only insert his or her finger into the test apparatus to a location at which a beam of light can be injected through the epidermis into the papillary bed that is closest to this portion of the epidermis.

In the preferred embodiment of a non-invasive blood component test apparatus, a person's finger is placed in contact with the test apparatus at a point where an light emitter focusses a beam of light into the finger and where one or more detectors detect light returning from the patient's finger. The measurement result can be affected by how hard a person presses his or her finger into contact with the test apparatus, because this can squeeze blood out of the finger, thereby decreasing the amount of blood glucose that is exposed by the exposing light and producing a spurious decrease in the apparent concentration of blood glucose. One or more additional sensors can be included in the test apparatus to measure light intensity at more than just 1040 cm$^{-1}$ to enable compensation for this change in pressure and to compensate for blackbody radiation intensity changes that result when a person's finger alters the temperature of the sensing apparatus. The wavelength of the exposing light is therefore selected to excite haemoglobin molecules sufficiently that the 1109 cm$^{-1}$ light emitted by such molecules will have sufficient intensity that the pressure-related changes in blood concentration in the papillary bed can be compensated for in the calculation of the blood glucose concentration. In order to compensate for such pressure-related changes in blood concentration within the papillary bed, the wavelength range of the exposing light is selected in the range from the narrower range 0.6–1.1 microns that not only can pass effectively through the epithelium, but is also effective in exciting haemoglobin molecules.

Because the haemoglobin concentration in patients can differ, a calibration measurement is required to determine, for a known blood glucose level, what that patient's haemoglobin concentration is. This is achieved by measuring a patient's blood glucose/haemoglobin concentration ratio with the present apparatus and, concurrently, drawing a sample of blood which is used to determine this ratio by any other convenient method.

The incident light is chopped in order to produce a pulsed output in the emitted light. This enables the use of synchronous detection to remove the approximately constant background from the pulsed emissions that carry information about the blood component concentration being measured.

In a blood component concentration detector embodiment, a transparent plate is included, against which a patient presses some portion of his or her epidermis, such as the front side of an index finger, during a blood component concentration test. One or more light beams containing at least one wavelength of light are focussed through this plate and through the epidermis of the patient's finger onto the portion of a papillary bed that is closest to the point of the epidermis at which this beam is directed through the epidermis. To keep background blackbody radiation substantially constant, this plate and surrounding components are maintained at a substantially constant temperature of 37° C. (normal body temperature), so that this temperature will not be substantially changed when the patient presses his or her finger into contact with this plate. Preferably, included in the exposing light are wavelength components that are characteristic of some other component of blood (e.g., haemoglobin) and of blackbody radiation, respectively, to enable corrections for measurement changes due to changes in the pressure of this finger against this plate and due to the temperature of this plate arising from contact with the patient's finger.

These and other advantages of the present invention will become clear from the detailed description given below in which a preferred embodiment is described in relation to the drawings. The detailed description is presented to illustrate the present invention, but is not intended to limit it.

DESCRIPTION OF THE PREFERRED EMBODIMENT

Figure 1:
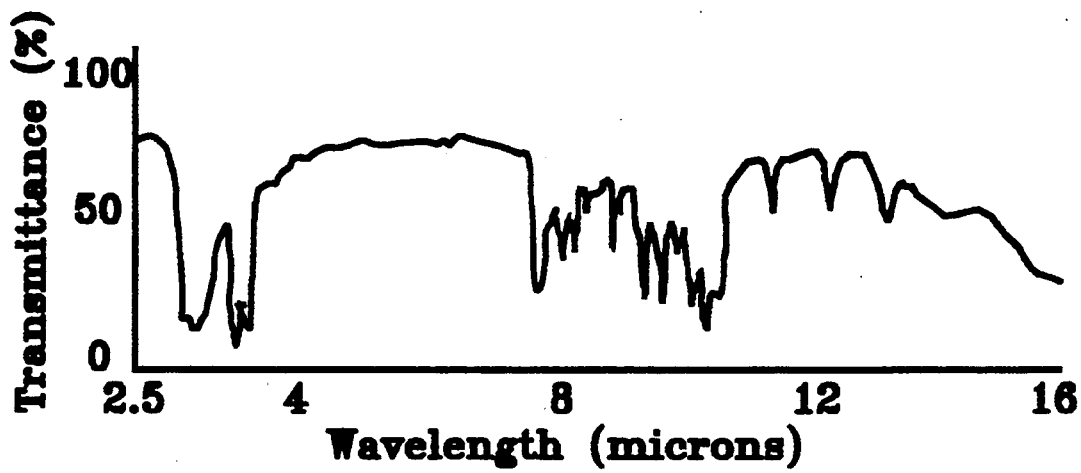
FIG. 1 illustrates the infrared absorption spectrum of anhydrous D-glucose.
Figure 2:
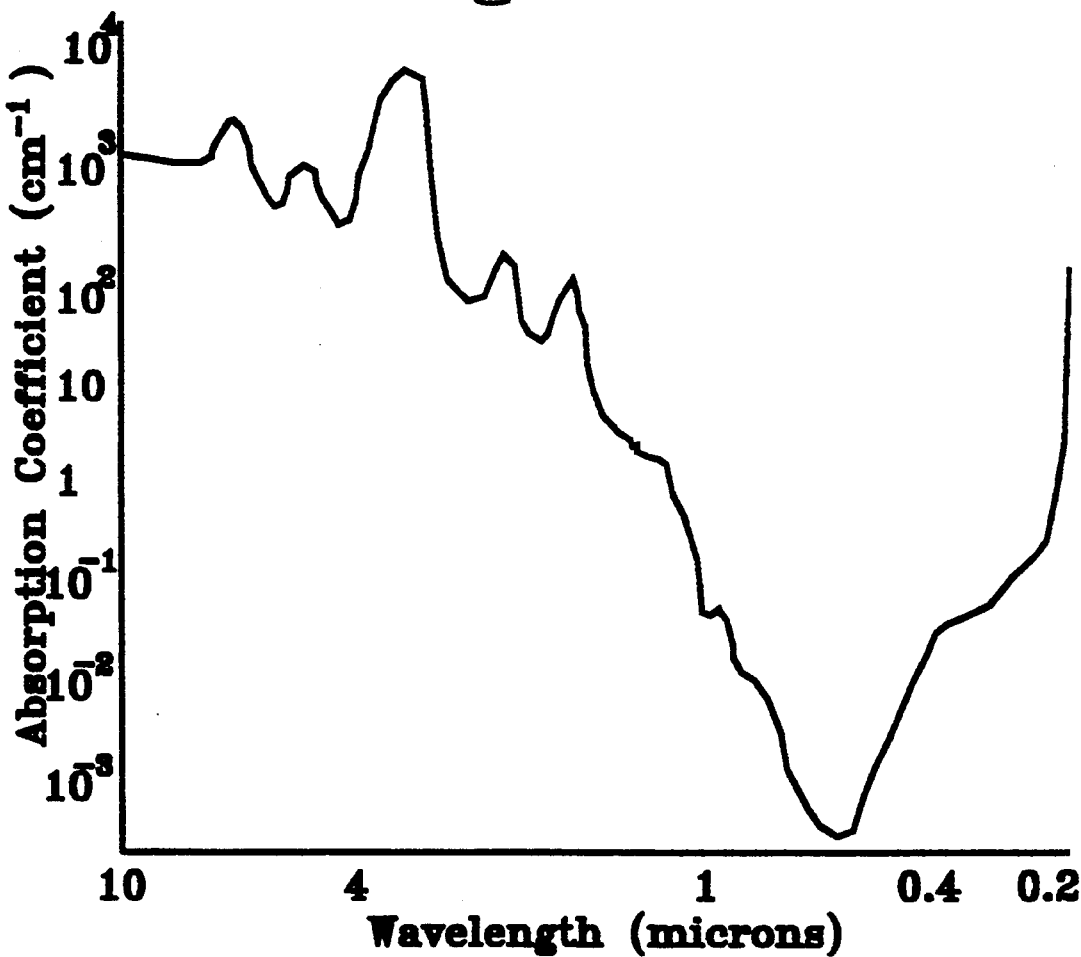
FIG. 2 illustrates the absorption spectrum of water as a function of wavelength.
Figure 3A:
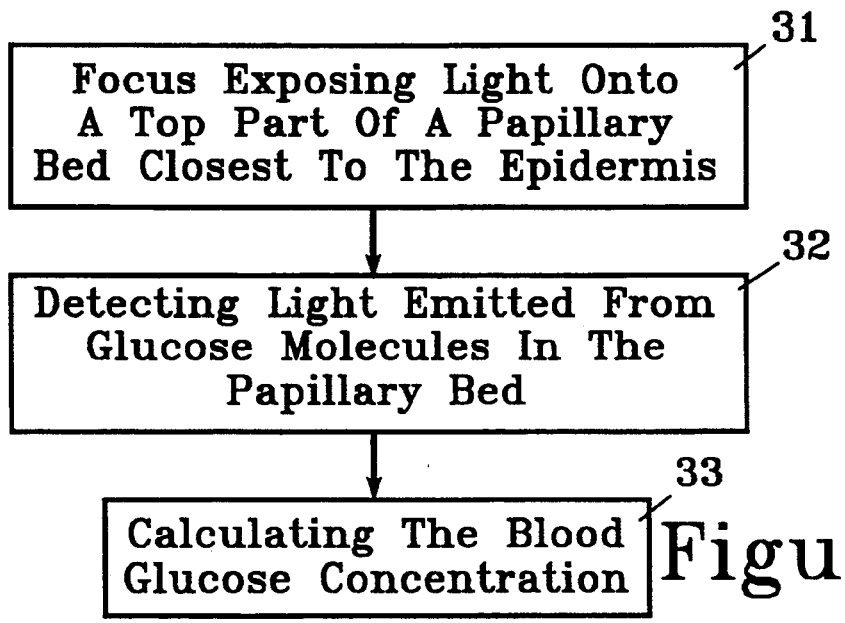
FIG. 3A is a flowchart of an improved method of detecting blood component concentrations.
Figure 3B:
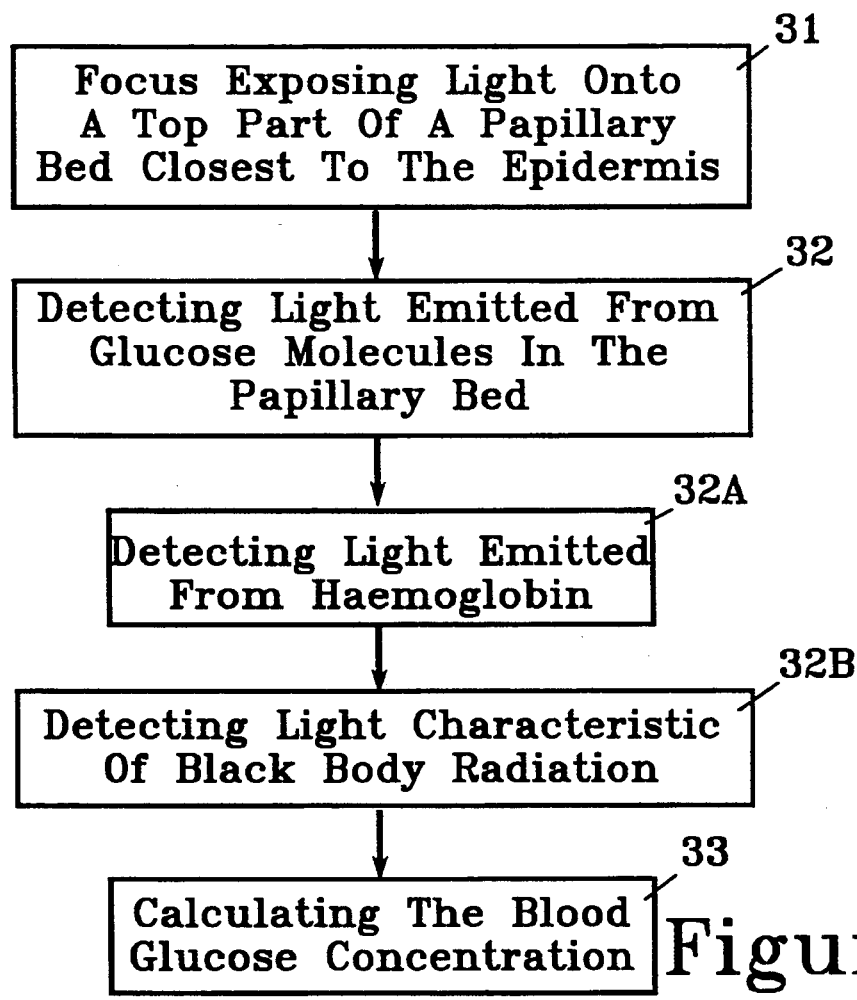
FIG. 3B illustrates an alternate embodiment of the method of FIG. 3A that enable compensation for pressure-related changes in a patient's blood concentration in the papillary bed and for temperature related changes in the blackbody radiation from the blood glucose concentration tester.
Figure 4:
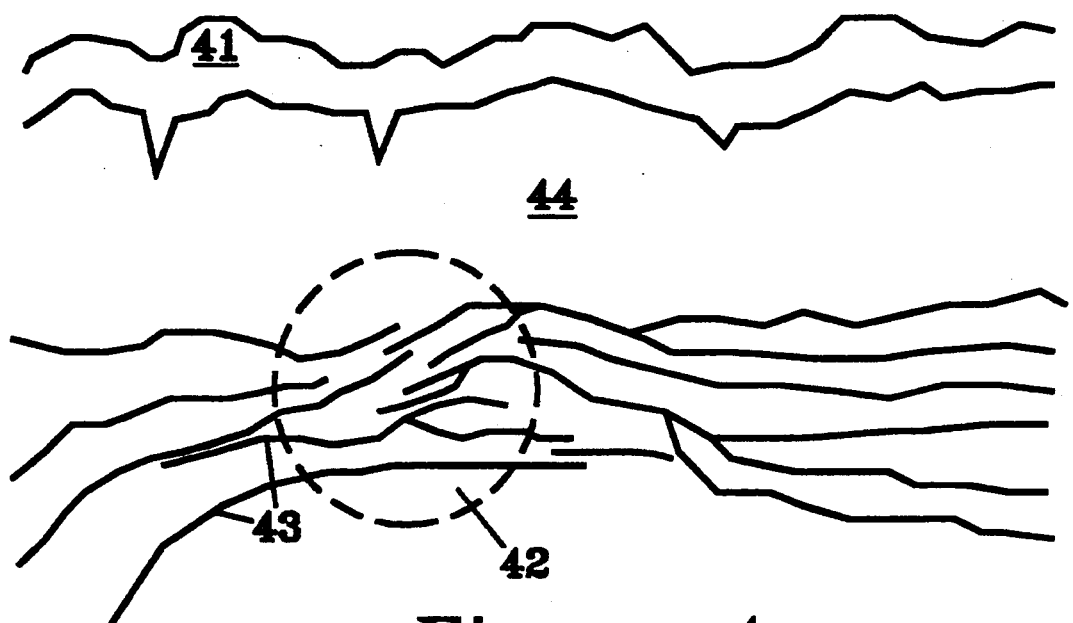
FIG. 4 illustrates the relationship between the epidermis of the skin of the fore finger, the dermis layer, the papillary bed and the blood vessels.

The invention will be illustrated for the case of a non-invasive, blood glucose concentration detector, but, as indicated above, this invention is also applicable to testing solute concentrations in many different types of solutions and in other environments, such as a sample contained within a test tube or smeared onto a slide. As outlined in FIG. 3A, in this process of measuring the concentration of a component of a blood sample, light of wavelength in the range from 0.6–1.5 microns is directed at a portion of a person or animal's epidermis to pass into a blood-rich region of that person or animal to excite the blood glucose molecules (also referred to an anhydrous D-glucose molecules, or ADG molecules) in the user's blood (step 31). As is illustrated in FIG. 4, this radiation is focussed, through the epidermis 41 of the front side of the index finger (i.e., the side that is opposite to the nail side of the finger) and a derm layer 44, to a point on the top part of the papillary bed 42 that is closest to the epidermis onto the papillary bed to excite the ADG molecules in blood vessels. This region is selected for exposure because it is a blood-rich region, having many blood vessels 43, closely spaced (about 0.3 mm) from the epidermis. Although any finger can be used, it is preferred that the least calloused finger be used to achieve improved penetration of the excitation radiation into that finger.

Figure 5:
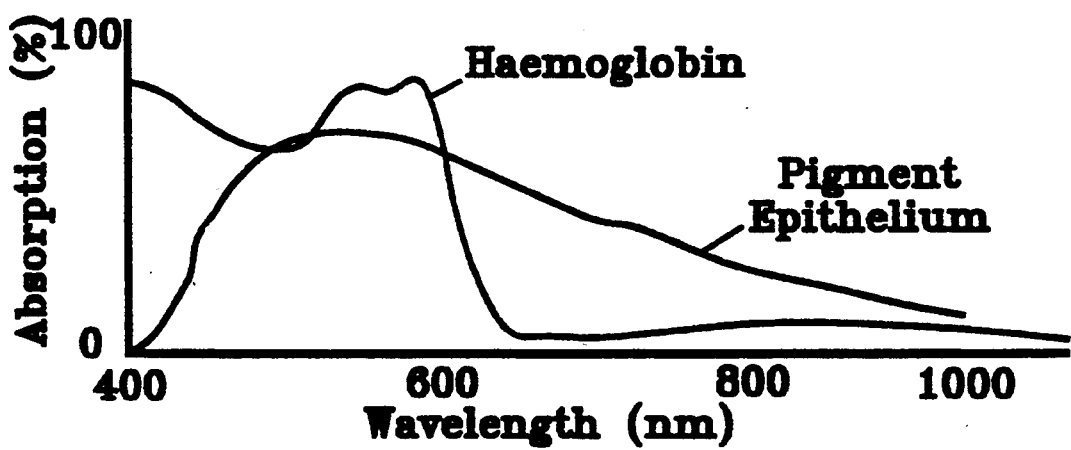
FIG. 5 illustrates the transmission spectrum of hemoglobin and pigment epithelium as a function of spectral wavelength.

The 0.6–1.5 microns (16,667–6,667 cm$^{-1}$) range is selected for the exposing light because it can pass, without significant attenuation, through the epidermis 41 (see FIG. 4). Preferably, the exposing light is within the range from 0.6–1.1 microns, because this range not only passes through the epidermis without undue attenuation, as illustrated in FIG. 5, it is also effective in exciting haemoglobin molecules, so that pressure-related changes in the amount of blood in papillary bed 42 can be compensated for from a knowledge of the amount of absorption by the haemoglobin molecules.

This exposing light not only excites blood glucose and haemoglobin molecules into an excited state, it also stimulates emission of light from such excited molecules. Because the incident light need only travel through about 0.3 mm of tissue, the exposing beam will not be significantly attenuated prior to exposing the blood in the papillary bed. Because the emitted light likewise need travel only through about 0.3 mm of tissue before incidence on a detector, it will likewise not be significantly attenuated. Because of this, the detected signal will be much larger than in prior techniques. The detected intensity of light is utilized to calculate the concentration of blood glucose (step 33). Examples of such calculations will be illustrated below.

Several optical sources, such as semiconductor LEDs and semiconductor laser diodes, can produce light at 0.6–1.5 or 0.6–1.1 microns. Because the probability of an ADG molecule's excitation in a beam of intensity on the order of 5 Watts/cm$^2$ is expected to be very small (typically around 10$^{-4}$ or smaller), it is important that the source of the exposing light emit adequate optical power in the right wavelength, in order to be effective as an excitation source. Because this exposing light plays the dual role of exciting blood glucose molecules into excited states and stimulating emission from such excited molecules, the rate of emission is proportional to the square of the intensity of this light. Therefore, the rate of emission is proportional to the square of the power of the excitation radiation. Therefore, it is advantageous to focus this light to onto a small area of the papillary bed 42. Preferably, this area has a diameter on the order of a few tens of microns, but diameters of up to 100 microns are also adequate. The depth of focus should also be on the order of the thickness, 100 microns, of the papillary bed. Semiconductor LEDs and semiconductor laser diodes typically have output powers in excess of 100 mW and higher and with proper delivery optics these output power levels are more than adequate for the currently disclosed blood glucose measurement technique. Super-radiant diodes are advantageous because of their particularly large beam intensity. An ultraviolet flashlamp could also be utilized as the light source.

It is advantageous for the optical source be substantially monochromatic, because monochromatic or substantially monochromatic light can be focussed onto a very tiny region with inexpensive optical components that do not correct for chromatic aberration. Such accurate focussing is needed to be able to focus this light accurately onto the top part of the papillary bed that is closest to the epidermis and to obtain the desired spot size. In addition, because the rate of emission is proportional to the square of the intensity of this light, such concentrated focussing of the light will greatly increase the rate of stimulated emission. Light emitting diodes (LEDs), emitting in the super-radiant mode, and semiconductor laser diodes meet all of these criteria for the optical source. Diode lasers of wavelength 0.67 microns are readily available with a bandwidth of 0.1 Å, FWHM. At a modest increase in cost, laser diodes having a bandwidth of 0.01 are also available. An additional advantage of such sources is that they are relatively inexpensive so that low cost, non-invasive blood glucose monitors can be produced.

Figure 6A:
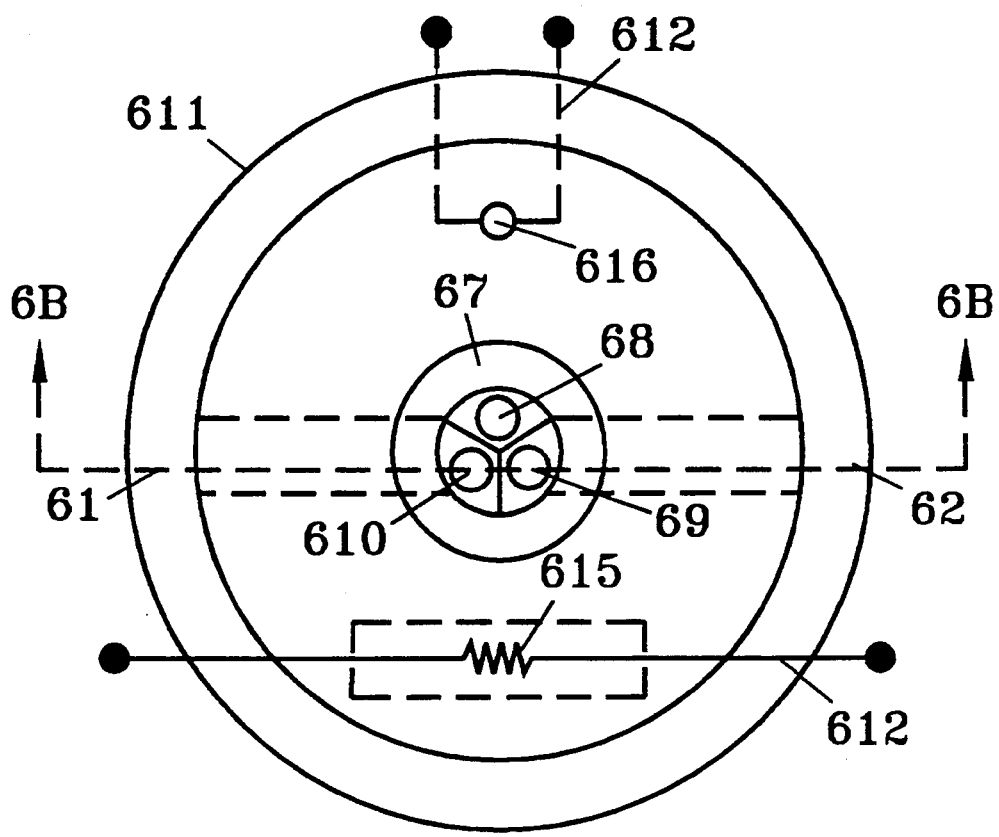
FIGS. 6A and 6B are a top plan view and a cross-sectional side view, respectively, of the preferred embodiment of a low-cost, non-invasive blood component concentrations tester.
Figure 6B:
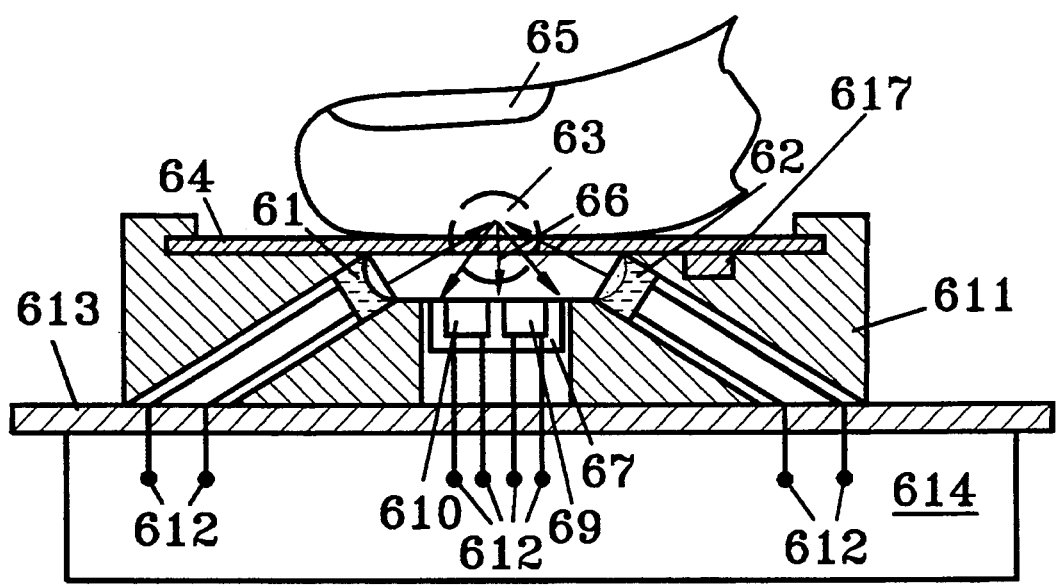

FIGS. 6A and 6B are top plan view and side cross-sectional views, respectively, of a first embodiment of a non-invasive, low-cost, blood glucose concentration detector. A pair of excitation light sources 61 and 62, such as LEDs or laser diodes, focus excitation radiation of wavenumber 1040 cm$^{-1}$ into a spatially small focal region 63 approximately 0.3 mm beyond an optically flat plate 64 that is transparent to both the excitation radiation and the subsequent relaxation emission radiation. Many choices of material, such as ZnS and ZnSe, are possible for this flat plate. This plate is "transparent" to light of a given wavelength if its obsorptivity is less than a few percent for such light.

During a blood glucose (also referred to as an anhydrous D-glucose, or ADG) concentration test, a user presses a front side (i.e., the side opposite to that person's nail) of his or her finger 65 against this plate, so that the excitation radiation beam can be accurately focussed onto the top of the papillary bed 42. This point of focus is chosen, because the numerous small blood vessels 43 within the papillary bed provide one of the closest locations of blood to a patient's epidermis and because a finger is conveniently pressed against plate 64 during testing. The ADG and haemoglobin molecules are excited by the excitation radiation and, upon returning to their ground states, emit radiation 66 that is characteristic of the ADG molecules. Although other wavelengths of relaxation radiation are also emitted by the ADG molecules, they are not uniquely emitted by ADG molecules and therefore are not as easily utilized to measure the concentration of ADG molecules.

Detector assembly 67 includes three infrared detectors 68, 69 and 610, each of which occupies about one-third of the total field of view subtended by the detector assembly 67 at the small focal region 63 of excitation radiation. Detectors 68, 69 and 610 are each housed in a separate compartment to prevent cross-talk or light leakage between them. Detectors 68, 69 and 610 each includes its own unique narrow band-pass interference filter passing only radiation at 1,040 cm$^{-1}$ (9.61 microns), 1,109 cm$^{-1}$ (9.02 microns) and 2,632 cm$^{-1}$ (3.80 micron), respectively. As will be explained in greater detail below, these choices of filters enable a measured concentration of ADG molecules to be produced that is unaffected by the temperature and touching pressure of the patient's finger.

The excitation light sources 61 and 62 and the detector assembly 67 are mounted inside a circular sensor housing 611 in such a way that a set of electrical leads 612 from the sources and detector assembly all come out from one side of detector assembly 67 opposite to that of the optical flat plate 64. Leads 612 can be conveniently soldered to a printed circuit board (PCB) 613 that contains processing electronic circuits 614 and also supports the overall sensor housing 611. The sensor housing 611 is temperature regulated at a temperature $T_0$ of approximately 37° C. (i.e., normal human body temperature) by means of a heater resistor 615 and a thermistor 616 imbedded therein. The electrical leads 612 of heater resistor 615 and thermistor 616 are also routed to the PCB 613 that also contains a temperature regulating circuit.

The narrow band-pass, interference filter included within detector 610 passes a narrow range of light centered at wavenumber 2,632 cm$^{-1}$ (wavelength 3.8 microns). This light is primarily blackbody radiation from the optical flat plate 64 and from those portions of detector assembly 67 immediate adjacent to this plate. The output of this detector provides information about any temperature changes caused by internal or external environmental changes, such as by the fore finger of the patient touching the optical flat plate during the blood glucose measurement itself. The relationship between the instantaneously measured signal from detector 610 and the instantaneous temperature T(t) measured in degree Celsius is given by $$I_s(t) = I_0 \times [(T(t)+273)/(T_0+273)]^4$$

where $I_2(t)$ is the instantaneous output signal of detector 610, $I_0$ is the output at $T_0$° C. and T(t)° C. is the instantaneous spatially averaged temperature of the cavity surrounding the detector assembly 67.

The narrow band-pass, interference filter included within detector 69 passes a narrow range of light centered at wavenumber 1,109 cm$^{-1}$ (wavelength 9.02 microns). Detector 69 receives radiation from three separate sources: (i) blackbody radiation from the cavity surrounding detector assembly 67 (which includes optical flat plate 64); (ii) relaxation radiation from hemoglobin inside the blood vessels; and (iii) relaxation radiation from the ADG molecules inside the blood vessels. As discussed in greater detail below, the output signal of detector 69 is needed to eliminate the effect of the variable touching pressure of the fore finger on the optical flat plate 64 during measurement, because the volume of blood and the quantity of hemoglobin in the blood vessels within the region exposed by the exposing light, is dependent of how hard the finger is pressed against optical flat plate 64. This blood volume is a function of this pressure because the touching pressure forces blood out of the capillary bed 42 in the region of the fore finger that is in contact with optical flat plate 64.

The narrow band-pass, interference filter included within detector 68 passes a narrow range of light centered at wavenumber 1,040 cm$^{-1}$ (wavelength 9.61 microns). Detector 68 receives radiation from two different sources: (i) relaxation radiation from the ADG molecules in the blood vessels; and (ii) blackbody radiation from the cavity surrounding detector assembly 67. The output signal of detector 68 therefore contains information relating to the amount of blood glucose in the blood vessels of the patient under test.

By processing the three signals received respectively from detectors 68, 69 and 610, a net output signal is produced that indicates the concentration of ADG molecules in the blood and is not affected by the temperature and touching pressure of the patient's finger on the optical fiat plate. This processing is well known from basic algebra. Let $I_s(t)$, $J_s(t)$ and $K_s(t)$ be the outputs, as a function of time t, of detectors 610, 69 and 68, respectively during a particular blood glucose measurement routine. $I_s(t)$ is a function of the instantaneous temperature T(t) of the cavity surrounding the detector assembly 67 including the optical flat plate 64. $J_s(t)$ is the sum of blackbody radiation at temperature T(t) and the relaxation radiation from hemoglobin and the ADG molecules in the blood vessels when these vessels are exposed by light from excitation light sources 61 and 62. $K_S(t)$ is the sum of the blackbody radiation at temperature $T(t)$ and the relaxation radiation from the ADG molecules when the latter is stimulated by the excitation light sources 61 and 62.

When no patient's finger is in contact with optical flat plate 64, the temperature of the cavity immediately surrounding the detector assembly 67 (including the optical flat plate) is regulated by thermistor 612 and heater resistor 615 to a temperature $T_0$ of 37° C. This temperature is selected because it should most closely match the actual temperature of a patient's finger. The outputs from detectors 610, 69 and 68 under this condition are represented as $I_0$, $J_0$ and $K_0$, respectively, and they represent only the blackbody radiation received at the wavelengths defined by the narrow band-pass filters of each of the respective detectors.

When the patient's finger touches the optical flat plate 64, the cavity and plate temperatures change to a slightly different temperature $T(t)$ and the outputs from the detectors 68, 69 and 610 are, respectively:

$$I_S(t) = I_0 \times [T(t)/T_0]^4 \quad \text{(Ia)}$$

$$J_S(t) = J_0 \times [T(t)/T_0]^4 + G[H(t)] + H(t) \quad \text{(Ib)}$$

$$K_S(t) = K_0 \times [T(t)/T_0]^4 + G[H(t)] \quad \text{(Ic)}$$

where $H(T)$ is the component of the output currents produced by relaxation radiation from haemoglobin molecules and $G[H(T)]$ is the component of the output currents produced by relaxation radiation from ADG molecules. $I_0$, $J_0$ and $K_0$ are known constants determined from measurements made when no patient's finger is present in the test apparatus. Measurement of the three parameters $I_S(t)$, $J_S(t)$ and $K_S(t)$ enables the three unknowns $H(t)$, $G[H(t)]$ and $T(t)$ to be determined by standard methods from basic algebra.

The amount of relaxation radiation from ADG molecules depends on the number of ADG molecules, which in turn is proportional to the blood volume being excited. The function $H(t)$ measures the relaxation radiation coming only from the haemoglobin molecules and is therefore a function of the blood volume being excited, which is why G is written as a function of $H(t)$. To first order in the pressure $P(t)$ $$H(t) = \Omega/P(t) \quad \text{(1)}$$

where $\Omega$ is a constant determined during a calibration procedure and where $P(t)$ is measured separately by a pressure sensor 617 before and during the blood glucose measurement.

In actual use of the non-invasive blood glucose concentration detector, the patient is guided to press his or her finger onto flat plate 64 with a pressure that is within a preselected pressure range. When the patient's finger applies pressure within this range, a green light is illuminated to indicate that this pressure is within the desired range. This range is selected to ensure that the volume of illuminated blood is within a range such that $H(t)$ can be accurately represented by equation (1) above.

Figure 7:
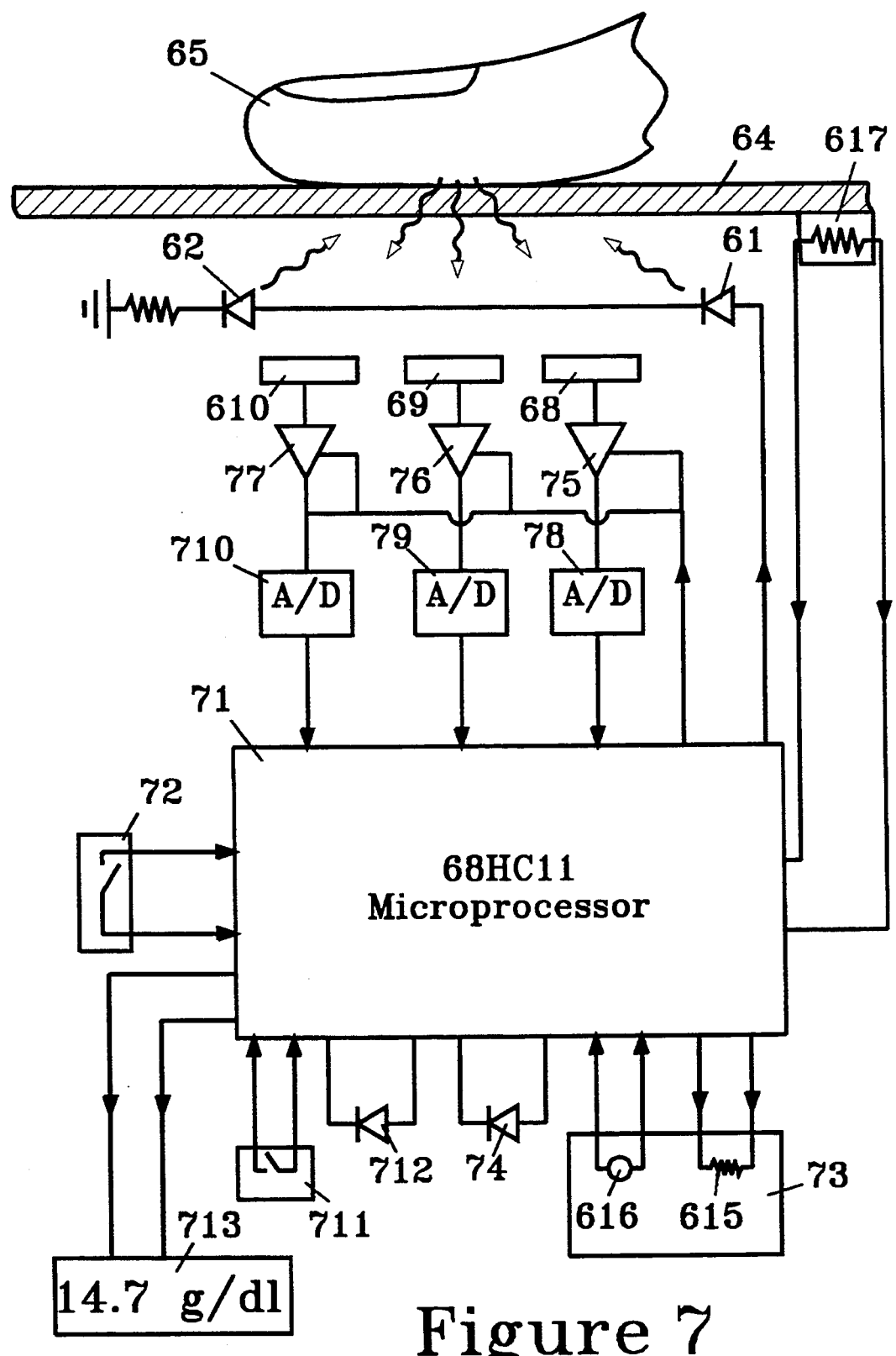
FIG. 7 is a block diagram of the signal processing components of the blood component sensor of FIGS. 6A and 6B.

The signal processing electronics of this blood glucose concentration detector is illustrated schematically in FIG. 7. A low-cost, low-power processor 71, such as the model 68HC11 single-chip, 16-bit microprocessor manufactured by Motorola, is used to control operation and to perform all calculations. When microprocessor 71 receives an ON signal from a manual ON/OFF switch 72, it activates temperature regulation circuitry 73 which controls the temperature of sensor housing 611 by means of heater resistor 615 and thermistor 612. When the temperature of sensor housing 611 reaches the preselected temperature $T_0$ (approximately 37° C.), a temperature ready light 74 is turned on and microprocessor 71 starts pulsing excitation light sources 61 and 62 at a frequency of F hertz (e.g., 60 Hz). Signals from detectors $I_S(t)$, $J_S(t)$ and $K_S(t)$ from detectors 68, 69 and 610, respectively, are amplified by preamplifiers 75-77 and A/D converters 78, 79 and 710, respectively. Because no finger is pressed against flat plate 64 at this point in the measurement process, the radiation detected by detector assembly 67 (which contains detectors 68, 69 and 610) is just blackbody radiation emanating from the sensor housing cavity, including the optical flat plate 64.

When microprocessor 71 receives an initialization signal from a manual switch 711, the outputs of A/D converters 78, 79 and 710 are stored and represent the values of $I_0$, $J_0$ and $K_0$, respectively. After the initialization routine has completed, a measurement ready light 712 begins to blink, indicating that the blood glucose concentration detector is ready. The patient is then to press his or her finger against flat plate 64. When pressure sensor 617 detects a pressure against flat plate 64 in the preselected pressure range, measurement ready light 712 converts from a blinking mode to a steady mode, thereby indicating that the actual blood glucose measurement has commenced. When the patient sees the measurement ready light 712 is steady, he or she should try to apply a constant pressure until light 712 begins blinking again. Changes in pressure should affect concentration measurements of ADG and haemoglobin substantially by the same multiplicative factor so that the ratio of ADG and haemoglobin concentrations is not significantly affected by changes in pressure during the measurement. Concurrently, a liquid crystal display (LCD) 713 displays the blood glucose concentration.

During the interval in which ready light 712 is steady, microprocessor 71 acquires the values $I_S(t)$, $J_S(t)$ and $K_S(t)$ and solves the three equations (Ia), (Ib), and (Ic) above to produce the value of the blood glucose concentration of the patient. At the end of this data acquisition and computation phase, measurement ready light 712 again begins to blink, thereby indicating that it is ready to perform another blood glucose concentration measurement. If desired, the patient can initiate another measurement simply by removing his or her finger from the optical flat plate, waiting for a couple of minutes and then repeating the measurement procedure. If at any time during a measurement, the pressure on flat plate 64 is outside of the preselected range, ready light 712 turns off and the measurement is voided.

Calibration of this low-cost, non-invasive blood glucose concentration detector is achieved by determining the value of $\Omega$ in equation (1) above. This can be done by a patient by measuring a sample of blood with the present blood glucose concentration detector and by concurrently drawing a sample of blood that in which the ratio of blood glucose concentration to haemoglobin concentration is determine by another blood glucose concentration detector that is known to be accurate. The ratio of these two values can be used by the patient to multiply the output of LCD 713 to produce an accurate concentration value. In some models, an input mechanism can be included that allows the user to input this ratio into microprocessor 71 so that this correction factor can be applied automatically by microprocessor 71. Alternatively, the user would have to take the value calculated by the instrument and scale it according to the results of the calibration measurement.

Figure 8A:
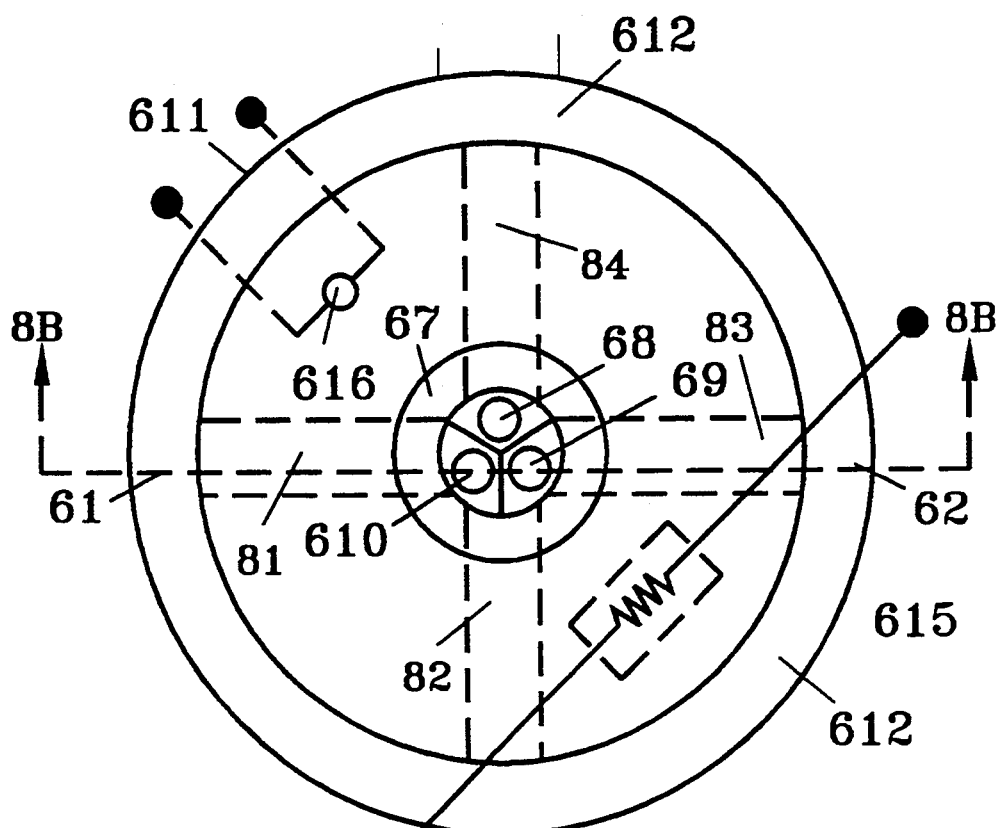
FIGS. 8A and 8B illustrate an alternate embodiment of the sensor of FIGS. 6A and 6B, having four optical sources.
Figure 8B:
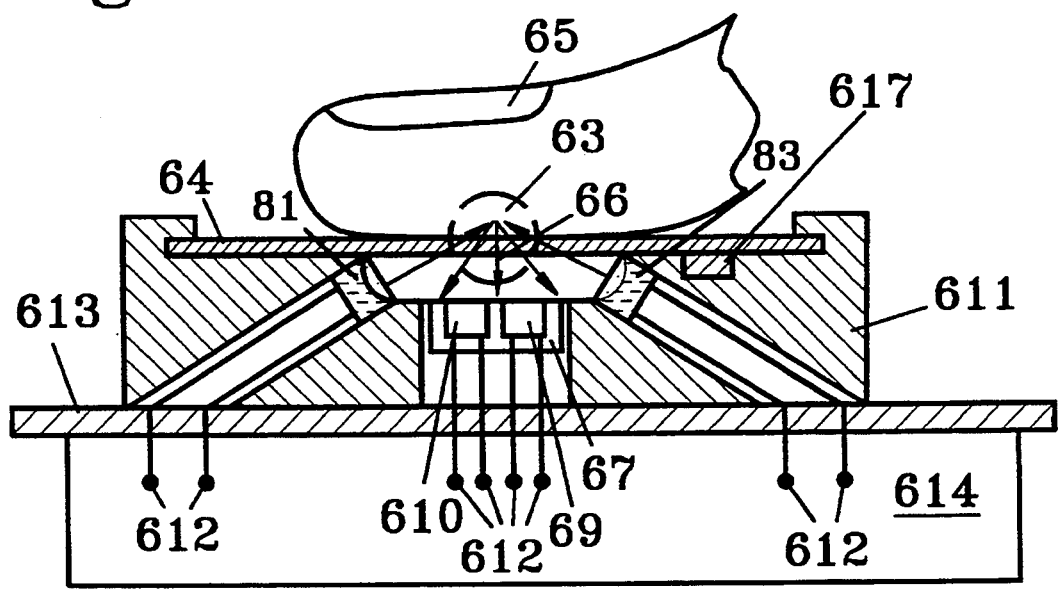

FIGS. 8A and 8B illustrate an alternate embodiment of sensor housing 611 that includes four excitation light sources 81–84 instead of two excitation light sources 61 and 62 as in the embodiment of FIG. 6. The use of four or more excitation light sources enhances the signal level of the relaxation radiation from both hemoglobin and ADG molecules, because of the resulting increase in excitation light energy density. This increases the signal-to-noise ratio of the emitted light received by detector assembly 67.

Figure 9A:
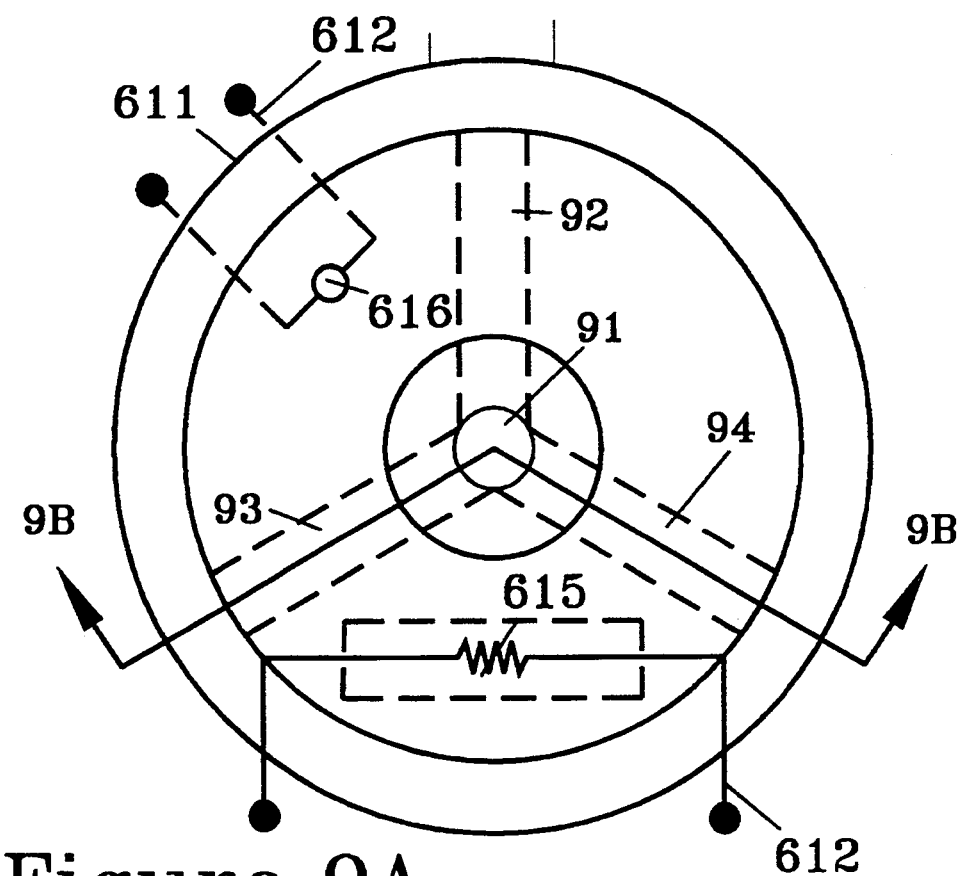
FIGS. 9A and 9B illustrate an alternative embodiment of the low-cost, non-invasive blood component sensor of FIGS. 6A and 6B, having three detectors spaced around a central optical source.
Figure 9B:
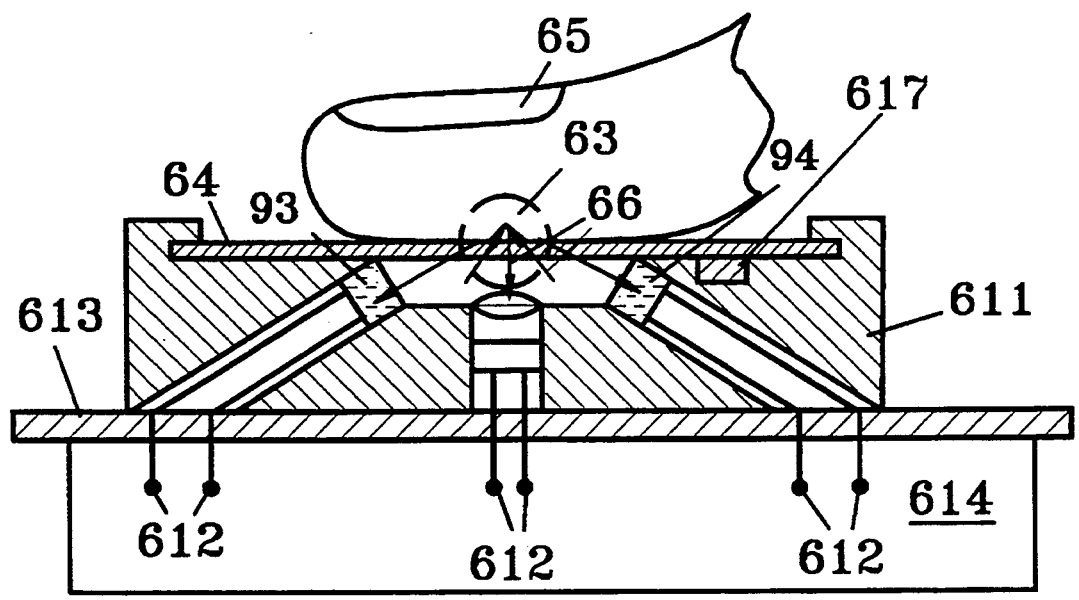

FIGS. 9A and 9B illustrate an alternate embodiment of the low-cost, non-invasive blood glucose concentration detector of FIGS. 6A and 6B, having three detectors spaced around a central optical source. A single excitation light source 91 is centered laterally within sensor housing 611. Excitation radiation is focussed by a relatively long focal length, achromatic doublet or triplet lens system onto a small focal region 63 just beyond optical flat plate 64. Three detectors 92–94 are located symmetrically about a central axis of sensor housing 611 to collect stimulated relaxation radiation from a patient's finger 65. Detectors 92–94 are each equipped with a different narrow band-pass, interference filter that passes radiation only at 9.61 microns (1,040 cm$^{-1}$), 9.02 microns (1,109 cm$^{-1}$) and 3.80 microns (2,632 cm$^{-1}$), respectively.

Figure 10A:
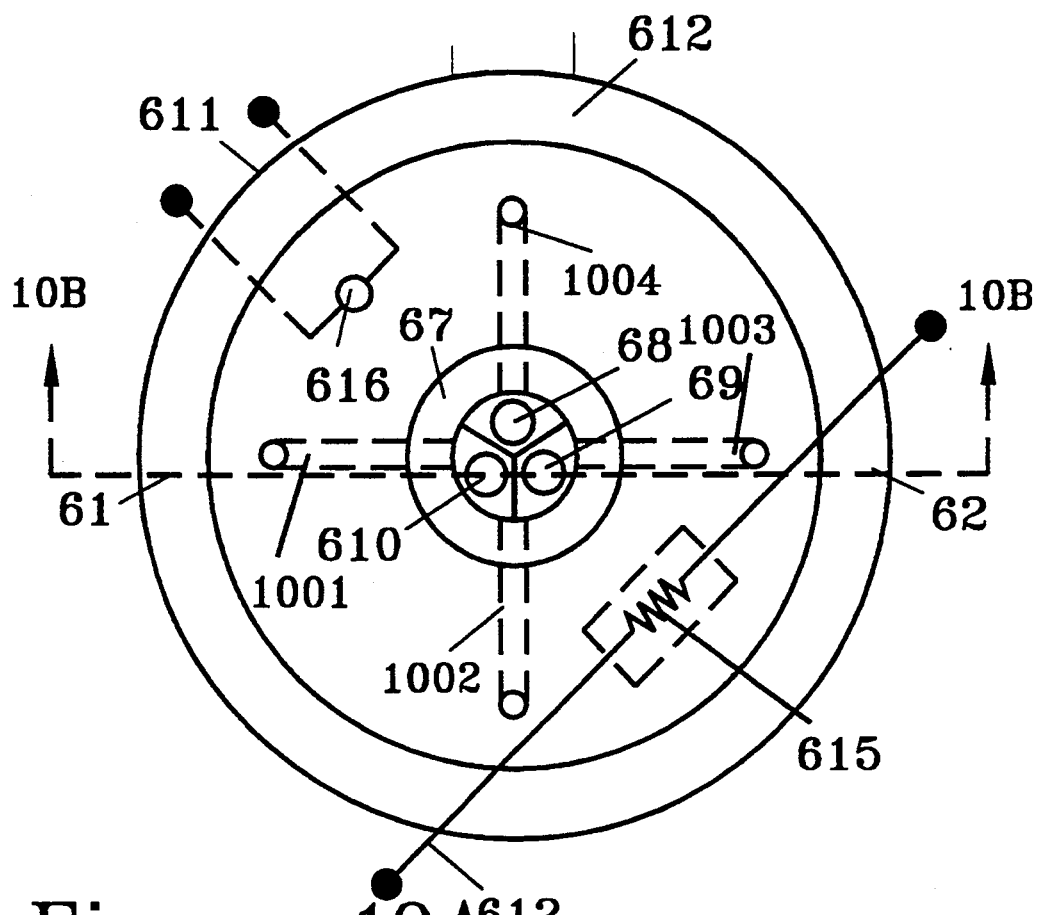
FIGS. 10A and 10B illustrate an alternate embodiment of the low-cost, non-invasive blood component sensor of FIGS. 6A and 6B, in which the source light is transmitted through a plurality of optical fibers.
Figure 10B:
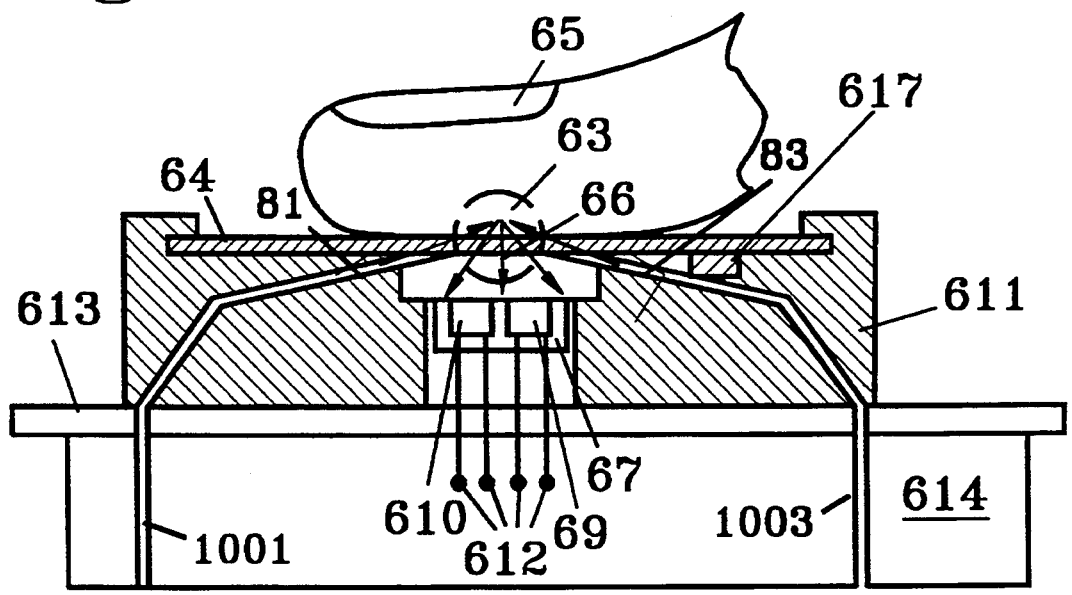

FIGS. 10A and 10B illustrate an alternate embodiment of the low-cost, non-invasive blood glucose concentration detector of FIGS. 6A and 6B. In place of the two excitation light sources 61 and 62 of the embodiment in FIGS. 6A and 6B are at least two optical fibers 1001–1004 arranged symmetrically about a longitudinal axis of sensor housing 611. This particular embodiment utilizes four such optical fibers. Excitation light is piped through the optical fibers and focussed onto a small focal region 63 just beyond the optical flat plate 64 as before. The use of optical fibers as the carriers of the excitation radiation enables the detector assembly 67, containing detectors 68, 69 and 610, to be mounted very close to focal region 63, thereby significantly increasing the solid angle within which these detectors receive light from focal region 63. This provides a concomitant increase in the signal to noise ratio of this concentration detector.

Figure 11A:
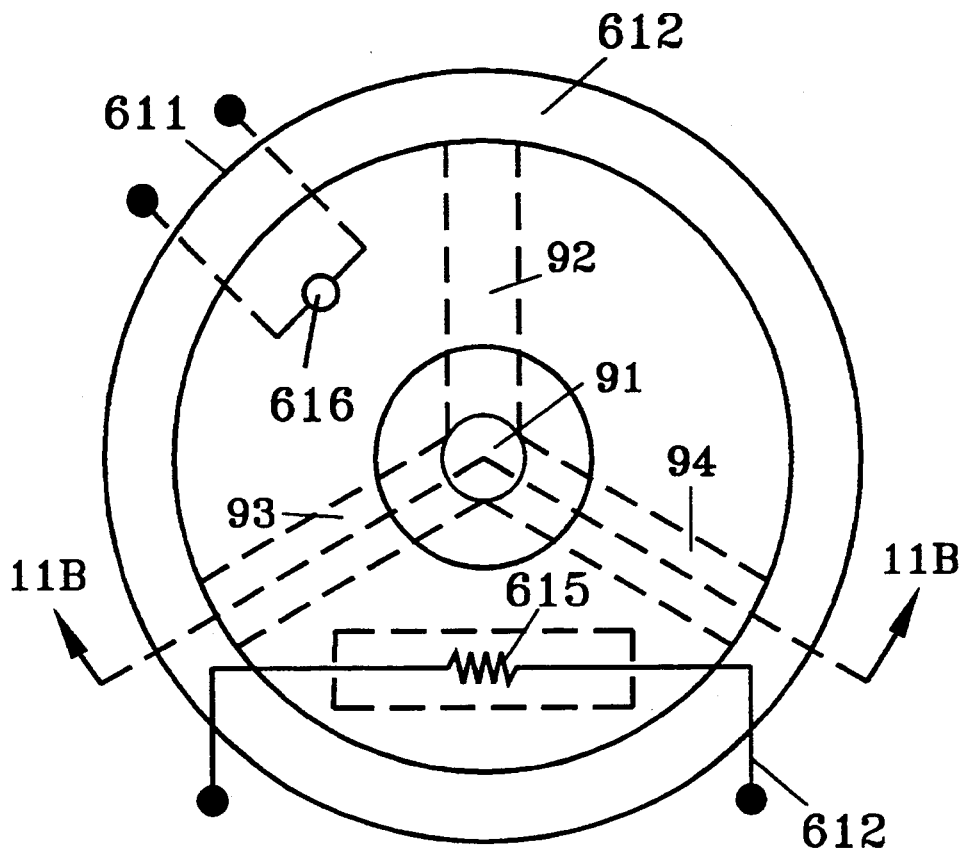
FIGS. 11A and 11B illustrate an alternative of the low-cost, non-invasive blood component sensor of FIGS. 6A and 6B, in which the source light is transmitted through a single optical fiber.
Figure 11B:
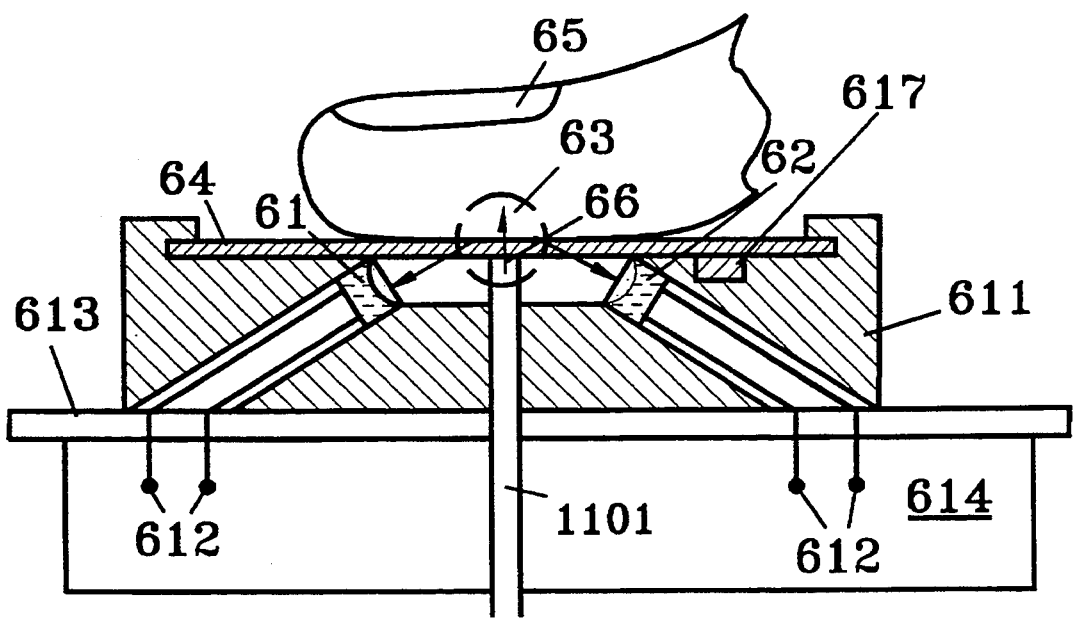

FIGS. 11A and 11B illustrate an alternate embodiment of the low-cost, non-invasive blood glucose concentration detector. The only difference between this embodiment and the embodiment of FIGS. 9A and 9B is that single excitation light source 91 is replaced by a single optical fiber 1101 that transports light from a remote location.

Figure 12A:
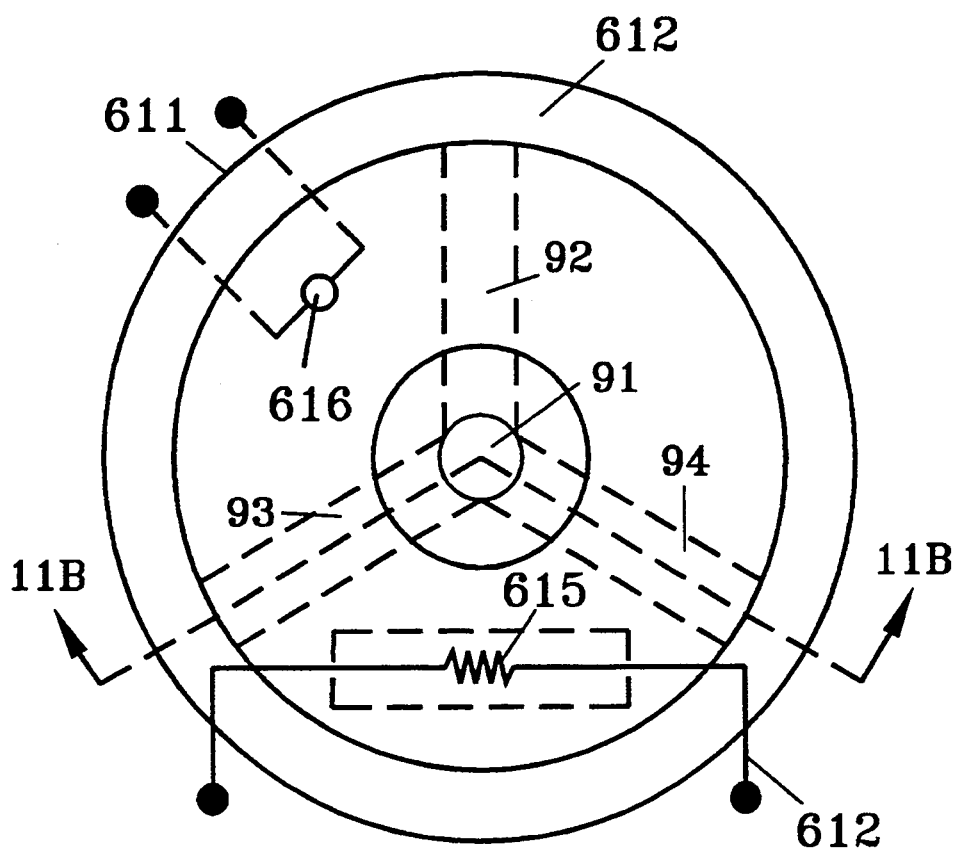
FIGS. 12A and 12B illustrate an alternative embodiment of the low-cost, non-invasive blood component sensor of FIGS. 11A and 11B, in which the single optical fiber penetrates the flat optical plate.
Figure 12B:
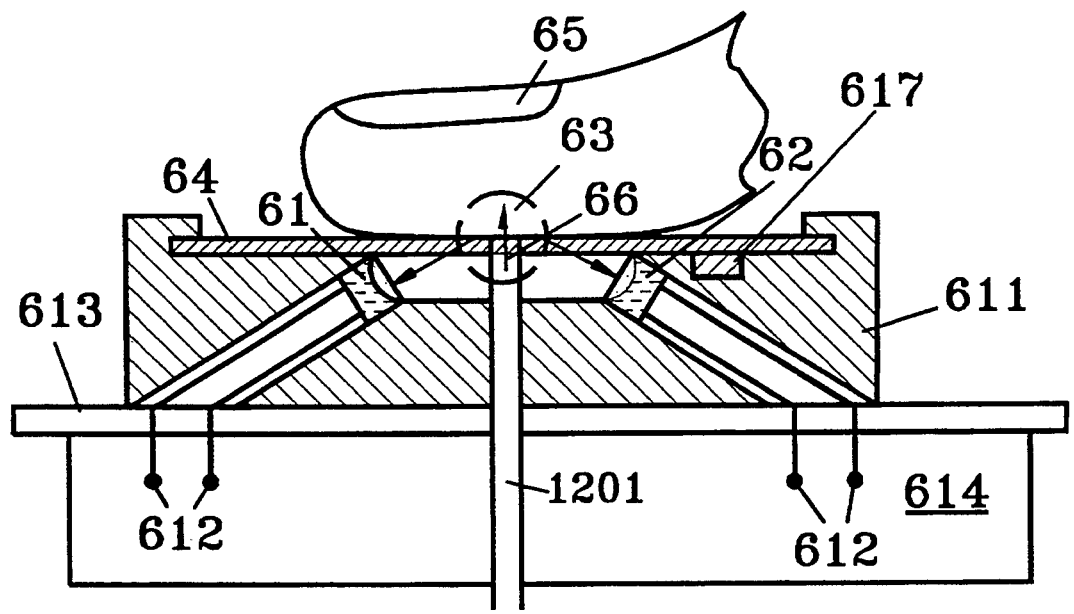

FIGS. 12A and 12B illustrate an alternate embodiment of the low-cost, non-invasive blood glucose concentration detector. In contrast to the embodiment of FIGS. 11A and 11B, optical fiber 1201 penetrates through optical flat plate 64. Because the excitation light does not now pass through optical flat plate 64, this plate can be made out of a different and less expensive material, such as silicon. Silicon blocks all radiation of wavelength less than about one micron, but has good transmission characteristics in the medium to far infrared. The other embodiments require that flat plate 64 be made of a material, such as ZnS or ZnSe, that transmits radiation from the visible all the way to the medium and far infrared. In general, ZnS and ZnSe plates are significantly more expensive than silicon plates.

The foregoing detailed description is illustrative of the invention and it is to be understood that additional embodiments thereof will be obvious to those skilled in the art. This description, together with those additional embodiments obvious to those skilled in the art, are considered to be within the scope of the invention.

We claim:

1. A non-invasive, blood chemistry measurement apparatus for measuring a concentration of a selected blood component within a sample of blood, said apparatus comprising:

a source of exposing light having a spectral peak at wavenumber $k_1$ that will excite said blood component to a state from which it emits light, by stimulated relaxation emission, having a peak at a second wavenumber $k_2$ different from $k_1$;

means for imaging said exposing light through an area of epidermis of an animal into a portion of that animal's blood adjacent to said area of epidermis on which this exposing light is incident;

means for detecting light that is emitted at wavenumber $k_2$ from molecules of said selected blood component in response to exposing light from said source of light; and means, responsive to said means for detecting, for calculating a concentration of said selected blood component.

2. An apparatus as in claim 1 wherein said means for detecting comprises a detector that is responsive substantially only to light at a wavenumber $k_2$ that is emitted by stimulated relaxation emission substantially only by molecules of said selected blood component.

3. An apparatus as in claim 1 wherein said means for detecting is responsive to a set of N different wavenumbers, thereby producing N signals $S_1, \ldots, S_N$, where N is greater than 1, wherein a first signal $S_1$ is produced in response to an associated stimulated relaxation emission peak from said selected blood component, wherein a second signal $S_2$ is produced in response to a different, associated stimulated emission peak from a second selected blood component and wherein said means for calculating a concentration is responsive to these N signals to produce the concentration of said selected blood component.

4. An apparatus as in claim 3 wherein said means for detecting detects only light in a set of N wavenumber bands and wherein each $S_k$, for $k=1, \ldots, N$, is proportional to the intensity of light in the kth of these wavenumber bands.

5. An apparatus as in claim 4 wherein said means for detecting comprises a set of N detectors, each of which detects light only in a uniquely associated one of these N wavenumber bands.

6. An apparatus as in claim 1 wherein said source of light is selected from the class consisting of a super-radiant photodiode and a flash lamp.

7. An apparatus as in claim 1 wherein the light from said source is imaged onto a region adjacent to said epidermis area of an animal and said means for detecting light comprises at least one optical detector positioned such that each ray of emitted light that is received by such at least one optical detector travels along a substantially minimum length path from its point of emission to such at least one detector, whereby absorption of emitted light by the solution is substantially minimized as a function of the position of said at least one detector.

8. An apparatus as in claim 7 wherein the light from said source is imaged onto a region within the animal and the light travels from said source to this region along a path that is substantially perpendicular to said epidermis area at a point that this light passes through such epidermis area, whereby the amount of absorption of this light by components of the solution other than said selected component is substantially minimized.

9. An apparatus as in claim 7 wherein the light has an intensity of at least 5 Watts/cm$^2$ within the region in which the light is imaged.

10. An apparatus as in claim 7 wherein said containment vessel is a finger of a human and the wall is a portion of the epidermis on a front surface of a finger of this human.

11. An apparatus as in claim 7 wherein said light from the source is directed onto a papillary bed in a subject under test.

12. An apparatus as in claim 11 wherein said light from the source is focussed onto this papillary bed.

13. A non-invasive, blood chemistry measurement apparatus for measuring a concentration of a selected blood component within a sample of blood, said apparatus comprising:
a source of exposing light having a spectral peak at wavenumber $k_1$ that will excite said blood component to a state from which it emits light, by stimulated relaxation emission, having a peak at a second wavenumber $k_2$ different from $k_1$;
means for imaging said exposing light through an area of epidermis of an animal into a portion of that animal's blood adjacent to said area of epidermis on which this exposing light is incident;
means for detecting light that is emitted at wavenumber $k_2$ from molecules of said selected blood component in response to exposing light from said source of light; and
means, responsive to said means for detecting, for calculating a concentration of said selected blood component, wherein N=2, wherein said selected blood component is blood glucose, wherein $S_1$ is proportional to an intensity of light within a band substantially centered on an emission peak of blood glucose substantially at a wavenumber of 1040 cm$^{-1}$, wherein $S_2$ is proportional to an intensity of light within a band substantially centered on an emission peak of haemoglobin produced by incident fight substantially at a wavenumber of 1109 cm$^{-1}$ and wherein said means for calculating a concentration calculates a concentration of blood glucose that is corrected by use of $S_2$ to take into account effects due to changes in blood volume intersected by the light from said light source.

14. A non-invasive, blood chemistry measurement apparatus for measuring a concentration of a selected blood component within a sample of blood, said apparatus comprising:
a source of exposing light having a spectral peak at wavenumber $k_1$ that will excite said blood component to a state from which it emits light, by stimulated relaxation emission, having a peak at a second wavenumber $k_2$ different from $k_1$;
means for imaging said exposing light through an area of epidermis of an animal into a portion of that animal's blood adjacent to said area of epidermis on which this exposing light is incident;
means for detecting light that is emitted at wavenumber $k_2$ from molecules of said selected blood component in response to exposing light from said source of light; and
means, responsive to said means for detecting, for calculating a concentration of said selected blood component,
wherein $S_1$ is proportional to an intensity of light within a band substantially centered on an emission peak of blood glucose substantially at a wavenumber of 1040 cm$^{-1}$, wherein $S_2$ is proportional to an intensity of light within a band substantially centered on an emission peak of haemoglobin produced by incident light substantially at a wavenumber of 1109 cm$^{-1}$, wherein $S_3$ is proportional to an intensity of light within a band that contains substantially only blackbody radiation from surrounding portions of this apparatus, and wherein said means for calculating a concentration calculates a concentration of blood glucose that is corrected by use of $S_2$ and $S_3$ to take into account effects due to changes in temperature and volume of blood intersected by the light from said source.

15. An apparatus as in claim 14 wherein light from the source includes a peak substantially, at 1109 cm$^{-1}$, whereby it is effective in substantially exciting haemoglobin molecules, whereby a measurement can be corrected to take into account a change in blood concentration being measured.

16. A non-invasive, blood chemistry measurement apparatus for measuring a concentration of a selected blood component within a sample of blood, said apparatus comprising:
a source of exposing light having a spectral peak at wavenumber $k_1$ that will excite said blood component to a state from which it emits light, by stimulated relaxation emission, having a peak at a second wavenumber $k_2$ different from $k_1$;
means for imaging said exposing light through an area of epidermis of an animal into a portion of that animal's blood adjacent to said area of epidermis on which this exposing light is incident;
means for detecting light that is emitted at wavenumber $k_2$ from molecules of said selected blood component in response to exposing light from said source of light;
means, responsive to said means for detecting, for calculating a concentration of said selected blood component;
a temperature sensor means for measuring a temperature of a region from which light is received by said means for detecting; and
means for maintaining a substantially constant, selected temperature T of a region of said apparatus that emits blackbody radiation to said means for detecting.

17. A non-invasive, blood chemistry measurement apparatus for measuring a concentration of a selected blood component within a sample of blood, said apparatus comprising:
a source of exposing light having a spectral peak at wavenumber $k_1$ that will excite said blood component to a state from which it emits light, by stimulated relaxation emission, having a peak at a second wavenumber $k_2$ different from $k_1$;

means for imaging said exposing light through an area of epidermis of an animal into a portion of that animal's blood adjacent to said area of epidermis on which this exposing light is incident;

means for detecting light that is emitted at wavenumber $k_2$ from molecules of said selected blood component in response to exposing light from said source of light;

means, responsive to said means for detecting, for calculating a concentration of said selected blood component;

a flat plate that is transparent to the emitted light, positioned such that light emitted from the sample of blood passes through this plate before reaching said means for detecting;

this plate providing a top surface against which a patient is to press a portion of the patient's epidermis during a blood test with this apparatus.

18. An apparatus as in claim 17 further comprising:
an optical fiber that penetrates through this flat plate and carries light from said source of light to said sample of blood;
said means for detecting is adjacent to this fiber and this plate.

19. An apparatus as in claim 17 further comprising:
an optical fiber that does not penetrate through said flat plate and which transports light from said source of light and directs this light through a portion of said flat plate at a point at which a patient is to press a portion of this patient's epidermis;
said means for detecting is adjacent to this fiber and this plate.

20. A non-invasive, blood chemistry measurement apparatus for measuring a concentration of a selected blood component within a sample of blood, said apparatus comprising:
a source of exposing light having a spectral peak at wavenumber $k_1$ that will excite said blood component to a state from which it emits light, by stimulated relaxation emission, having a peak at a second wavenumber $k_2$ different from $k_1$;
means for imaging said exposing light through an area of epidermis of an animal into a portion of that animal's blood adjacent to said area of epidermis on which this exposing light is incident;
means for detecting light that is emitted at wavenumber $k_2$ from molecules of said selected blood component in response to exposing light from said source of light;
means, responsive to said means for detecting, for calculating a concentration of said selected blood component; and
a flat plate, that is transparent to the emitted light, positioned such that light emitted from the sample of blood passes through this plate before reaching said means for detecting;
this plate providing a top surface against which a patient is to press a portion of the patient's epidermis during a blood test with this apparatus;
wherein said flat plate is of a material selected from the class consisting of ZnS and ZnSe.

21. An apparatus as in claim 17 further comprising:
a pressure sensor means, in contact with said flat plate, for measuring a pressure of said patient's epidermis against this plate;
said means for calculating being responsive to a pressure measured by this pressure sensor to correct the calculated concentration of said selected blood component to take into account an effect of this pressure on this calculated concentration.

22. A method of measuring the concentration of a selected blood component of an animal, said method comprising the steps of:
(a) directing, through an epidermis of said animal, exposing light having at least one wavenumber selected to excite said selected blood component to emit light of wavenumber characteristic of that component;
(b) detecting light that is emitted from said selected blood component in response to the exposing light which has a peak wavelength that produces stimulated emission of light from said selected blood component; and
(c) calculating a concentration of said selected blood component.

23. A method as in claim 22 wherein said exposing light is imaged onto a papillary bed, wherein there is a rich supply of blood glucose.

24. A method as in claim 23 wherein the exposing light is substantially monochromatic, whereby the exposing light can be strongly concentrated onto the papillary bed.

25. A method as in claim 22 wherein step (b) comprises the steps of:
(b1) detecting emitted light at a first wavenumber $k_1$ at which there is a significant level of emission from said selected blood component and from a second blood component;
(b2) detecting emitted light at a second wavenumber $k_2$ at which at least one of the selected blood component and the second blood component exhibits an emission peak; and
wherein step (c) calculates a concentration for the selected blood component, utilizing the detected intensities at wavenumbers $k_1$ and $k_2$.

26. A method as in claim 22, wherein, in step (a), a portion of the epidermis through which the exposing light is directed is contained on a front surface of a person's finger.

27. A method of measuring the concentration of a selected blood component of an animal, said method comprising the steps of:
(a) directing, through an epidermis of said animal, exposing light having at least one wavenumber selected to excite said selected blood component to emit light of wavenumber characteristic of that component;
(b) detecting light that is emitted from said selected blood component in response to the exposing light; and
(c) calculating a concentration of said selected blood component,
wherein the exposing light is in the range from 0.6–1.5 microns, whereby a ratio of the absorbance by blood glucose to the total absorbance by blood haemoglobin and the animal's epidermis is increased.

28. A method of measuring the concentration of a selected blood component of an animal, said method comprising the steps of:
(a) directing, through an epidermis of said animal, exposing light having at least one wavenumber selected to excite said selected blood component to emit light of wavenumber characteristic of that component;

(b1) detecting emitted light at a first wavenumber $k_1$ at which there is a significant level of emission from said selected blood component and from a second blood component;

(b2) detecting emitted light at a second wavenumber $k_2$ at which at least one of the selected blood component and the second blood component exhibits an emission peak; and (b3) detecting light at a wavenumber $k_3$ at which there is a significant level of blackbody radiation;

(c) calculating a concentration of said selected blood component utilizing the detected intensities at wavenumbers $k_1$, $k_2$ and $k_3$.

29. A method of measuring the concentration of a selected blood component of an animal, said method comprising the steps of:

(a) directing, through an epidermis of said animal, exposing light having at least one wavenumber selected to excite said selected blood component to emit light of wavenumber characteristic of that component, wherein a portion of the epidermis through which the exposing light is directed is contained on a front surface of a person's finger;

(b) detecting light that is emitted from said selected blood component in response to the exposing light Which has a peak wavelength that produces stimulated emission of light from said selected blood component; and (c) calculating a concentration of said selected blood component, wherein the portion of epidermis through which the exposing light is directed is pressed into contact with a window through which said exposing light is directed, said method further comprising the step of:

(d) sensing a pressure of contact between the window and the portion of the epidermis through which the exposing light is directed; and, in step (c)

adjusting the calculated concentration of the selected blood component, taking into account the effect of pressure on the measured intensities.

* * * * *